(12) United States Patent
Forester et al.

(10) Patent No.: US 11,920,299 B2
(45) Date of Patent: Mar. 5, 2024

(54) FORMATION DETECTION SYSTEM AND A PROCESS OF CONTROLLING

(71) Applicant: IBS of America, Chesapeake, VA (US)

(72) Inventors: Andrew Forester, Schoolcraft, MI (US); Paul Wratschko, Chesapeake, VA (US); Jake Neal, Virginia Beach, VA (US); David Jackson, Chesapeake, VA (US); Chris Blair, Chesapeake, VA (US); James Faufau, Jasper, GA (US)

(73) Assignee: IBS of America, Chesapeake, VA (US)

( * ) Notice: Subject to any disclaimer, the term of this patent is extended or adjusted under 35 U.S.C. 154(b) by 214 days.

(21) Appl. No.: 17/181,612

(22) Filed: Feb. 22, 2021

(65) Prior Publication Data
US 2021/0277601 A1 Sep. 9, 2021

Related U.S. Application Data

(60) Provisional application No. 62/986,239, filed on Mar. 6, 2020.

(51) Int. Cl.
*D21F 5/04* (2006.01)
*G01N 21/89* (2006.01)
*G01N 33/34* (2006.01)

(52) U.S. Cl.
CPC .............. *D21F 5/04* (2013.01); *G01N 21/89* (2013.01); *G01N 33/346* (2013.01)

(58) Field of Classification Search
CPC . D21F 5/04; D21F 9/006; D21F 11/04; D21F 9/02; G01N 21/89; G01N 33/346;
(Continued)

(56) References Cited

U.S. PATENT DOCUMENTS 1,712,632 A    5/1929   Peterson et al.
2,305,300 A   12/1942   Lowe
(Continued)

FOREIGN PATENT DOCUMENTS

CN    102650922 A    8/2012
CN    104512336 A    4/2015
(Continued)

OTHER PUBLICATIONS

Co-Pending U.S. Appl. No. 15/075,502, filed Mar. 21, 2016. (1734. 001 USC3).
(Continued)

*Primary Examiner* — Jose A Fortuna
(74) *Attorney, Agent, or Firm* — Young Basile Hanlon & MacFarlane, P.C.

(57) ABSTRACT

A formation detection system comprising: (a) one or more sensors and (b) one or more lights that illuminate a location of interest so that the one or more sensors can monitor the location of interest; wherein one of the one or more sensors are located substantially planar with a wire of a paper machine and proximate to a slice opening so that the one of the one or more sensors is adjacent to a cut through so that the one of the one or more sensors is capable of measuring stock above the wire and removed water below the wire, and wherein the one of the one or more sensors is capable of measuring a distance between an impingement location of a stock jet and the wire from a forming board.

12 Claims, 17 Drawing Sheets

(58) Field of Classification Search
CPC .......... G01N 33/34; G01N 21/86; D21G 9/00; D21G 9/0009; D21G 9/0036
See application file for complete search history.

(56) References Cited

U.S. PATENT DOCUMENTS

| | | | |
|---|---|---|---|
| 3,196,072 A | 7/1965 | Wirtz | |
| 3,405,031 A | 10/1968 | Sisson | |
| 3,419,723 A | 12/1968 | Germans et al. | |
| 3,469,104 A | 9/1969 | Hector | |
| 3,534,402 A | 10/1970 | Crowell et al. | |
| 3,573,159 A | 3/1971 | Sepall | |
| 3,607,624 A | 9/1971 | Moody et al. | |
| 3,922,190 A | 11/1975 | Cowan | |
| 4,019,819 A | 4/1977 | Lodzinski | |
| 4,124,441 A | 11/1978 | Nykopp | |
| 4,198,139 A | 4/1980 | Payne | |
| 4,443,298 A | 4/1984 | Thorp | |
| 4,500,968 A | 2/1985 | Bialkowski | |
| 4,644,174 A | 2/1987 | Ouellette et al. | |
| 4,730,931 A | 3/1988 | Watson | |
| 4,738,751 A | 4/1988 | Newcombe | |
| 4,838,996 A | 6/1989 | Kallmes | |
| 4,841,223 A | 6/1989 | Baum et al. | |
| 4,857,747 A | 8/1989 | Bolton et al. | |
| 4,931,657 A | 6/1990 | Houston et al. | |
| 4,939,929 A | 7/1990 | Ostman | |
| 4,955,720 A | 9/1990 | Blecha et al. | |
| 4,968,387 A | 11/1990 | Beran et al. | |
| 4,974,261 A | 11/1990 | Nakahara et al. | |
| 5,011,573 A | 4/1991 | Niemi | |
| 5,045,154 A | 9/1991 | Baluha | |
| 5,080,760 A | 1/1992 | Smith et al. | |
| 5,113,454 A | 5/1992 | Marcantonio et al. | |
| 5,169,500 A | 12/1992 | Mejdell | |
| 5,239,376 A | 8/1993 | Dittmann et al. | |
| 5,269,884 A | 12/1993 | Peterson | |
| 5,298,127 A | 3/1994 | Beran | |
| 5,302,250 A | 4/1994 | Peterson et al. | |
| 5,305,392 A | 4/1994 | Longest, Jr. et al. | |
| 5,331,408 A | 7/1994 | Jordan et al. | |
| 5,472,571 A | 12/1995 | Niemi | |
| 5,492,601 A | 2/1996 | Ostermayer et al. | |
| H1616 H | 12/1996 | Wolfe | |
| 5,654,799 A * | 8/1997 | Chase .................... | G01N 21/86 356/600 |
| 5,717,456 A | 2/1998 | Rudt et al. | |
| 5,776,309 A | 7/1998 | Fraik | |
| 5,830,322 A | 11/1998 | Cabrera y Lopez Caram et al. | |
| 5,922,173 A | 7/1999 | Neun et al. | |
| 5,951,823 A | 9/1999 | Cabrera Y Lopez Caram et al. | |
| 6,030,501 A | 2/2000 | Neun et al. | |
| 6,053,040 A | 4/2000 | Callender et al. | |
| 6,126,786 A | 10/2000 | White et al. | |
| 6,129,817 A | 10/2000 | Rule, Jr. | |
| 6,146,502 A | 11/2000 | Marx | |
| 6,290,816 B1 | 9/2001 | Graf | |
| 6,301,373 B1 | 10/2001 | Bernie et al. | |
| 6,362,889 B1 | 3/2002 | Mustonen | |
| 6,444,094 B1 | 9/2002 | Rulis et al. | |
| 6,470,598 B2 | 10/2002 | Ringer | |
| 6,702,925 B2 | 3/2004 | Bricco et al. | |
| 6,743,337 B1 | 6/2004 | Ischdonat | |
| 6,799,083 B2 | 9/2004 | Chen et al. | |
| 6,873,353 B1 | 3/2005 | Valkonen et al. | |
| 6,982,025 B2 | 1/2006 | Pitt | |
| 6,988,018 B2 | 1/2006 | Eames | |
| 7,101,461 B2 * | 9/2006 | Allen .................... | G01N 21/86 356/429 |
| 7,169,262 B2 | 1/2007 | Bricco et al. | |
| 7,318,882 B2 | 1/2008 | Niemi | |
| 7,545,971 B2 * | 6/2009 | Shakespeare ........ | G01B 11/306 382/141 |
| 7,695,592 B2 | 4/2010 | Shakespeare et al. | |
| 7,993,492 B2 | 8/2011 | Cabrera Y Lopez Caram | |
| 8,236,139 B1 | 8/2012 | Reed | |
| RE43,679 E | 9/2012 | Van Essen et al. | |
| 8,325,225 B2 | 12/2012 | Brenneman et al. | |
| 8,551,293 B2 | 10/2013 | Faufau et al. | |
| 8,685,209 B2 | 4/2014 | Faufau et al. | |
| 8,951,389 B2 | 2/2015 | Faufau et al. | |
| 9,045,859 B2 | 6/2015 | Gauss et al. | |
| 9,739,012 B1 * | 8/2017 | Forbes ................ | D21G 9/0009 |
| 9,841,383 B2 | 12/2017 | Ribnick et al. | |
| 10,280,561 B2 | 5/2019 | Heaven et al. | |
| 11,231,363 B2 * | 1/2022 | Shitara ................... | H04N 23/56 |
| 2002/0100569 A1* | 8/2002 | Allen ................... | G01N 33/346 162/198 |
| 2003/0051843 A1 | 3/2003 | Keller et al. | |
| 2003/0116295 A1 | 6/2003 | Eames | |
| 2004/0069059 A1* | 4/2004 | Shakespeare ........ | D21G 9/0009 73/159 |
| 2004/0112560 A1 | 6/2004 | Yamashita et al. | |
| 2005/0008765 A1 | 1/2005 | Karjanmaa | |
| 2005/0139339 A1 | 6/2005 | Niemi | |
| 2005/0150627 A1 | 7/2005 | Frawley et al. | |
| 2006/0096726 A1 | 5/2006 | Ahvenainen et al. | |
| 2006/0237156 A1* | 10/2006 | Shakespeare ........ | G01N 21/898 356/429 |
| 2007/0078557 A1 | 4/2007 | Finn et al. | |
| 2008/0013818 A1* | 1/2008 | Shakespeare .......... | G06T 7/001 162/263 |
| 2010/0066826 A1 | 3/2010 | Munch | |
| 2011/0050879 A1 | 3/2011 | Shyy | |
| 2011/0186254 A1 | 8/2011 | Cabrera Y Lopez Caram | |
| 2013/0042987 A1 | 2/2013 | Cabrera Y Lopez Caram | |
| 2015/0225897 A1 | 8/2015 | Forester et al. | |
| 2016/0201262 A1 | 7/2016 | Faufau et al. | |
| 2017/0067206 A1 | 3/2017 | Forester et al. | |
| 2017/0241078 A1* | 8/2017 | Forbes ................ | G06T 7/0004 |
| 2018/0142412 A1 | 5/2018 | Heaven et al. | |
| 2021/0108369 A1* | 4/2021 | Jones ...................... | D21F 7/008 |
| 2021/0223171 A1* | 7/2021 | Shitara ............... | G01N 21/3559 |
| 2021/0277601 A1* | 9/2021 | Forester ................ | D21F 11/04 |
| 2022/0191353 A1* | 6/2022 | Sekiya ................... | G03B 17/55 |

FOREIGN PATENT DOCUMENTS

| | | | |
|---|---|---|---|
| CN | 205443769 U | 8/2016 | |
| CN | 105960261 A | 9/2016 | |
| DE | 102005036482 A1 | 2/2007 | |
| DE | 102008059681 A1 | 6/2009 | |
| EP | 0837323 A2 | 4/1998 | |
| EP | 1314669 A2 | 5/2003 | |
| EP | 1548187 A2 | 6/2005 | |
| EP | 1548399 A1 | 6/2005 | |
| EP | 1749930 A1 * | 2/2007 | .......... D21G 1/0073 |
| EP | 2907918 A1 | 8/2015 | |
| EP | 3875683 A1 * | 9/2021 | ............. D21F 11/04 |
| EP | 3951490 A1 * | 2/2022 | ............. G03B 17/02 |
| JP | H01246490 A | 10/1989 | |
| JP | H0465594 A | 3/1992 | |
| JP | H07122616 B2 * | 7/1995 | ............. G01N 21/89 |
| JP | 20022511536 A | 4/2002 | |
| JP | 2003328288 A | 11/2003 | |
| RU | 2019129149 A | 12/2019 | |
| TW | M520542 U | 4/2016 | |
| WO | 9119186 A1 | 12/1991 | |
| WO | 99/53134 A1 | 10/1999 | |
| WO | 2000/045156 A1 | 8/2000 | |
| WO | 2002/046523 A1 | 6/2002 | |
| WO | 2002/061203 A2 | 8/2002 | |
| WO | 2003/081219 A1 | 10/2003 | |
| WO | 2007/088456 A2 | 8/2007 | |
| WO | 2008/118303 A1 | 10/2008 | |
| WO | 2010/094495 A1 | 8/2010 | |
| WO | 2019229919 A1 | 12/2019 | |

OTHER PUBLICATIONS

Co-Pending U.S. Appl. No. 15/354,179, filed Nov. 17, 2016. (1734.005USC1).

(56) References Cited

OTHER PUBLICATIONS

Peterson, R. S., "Improving Basis Weight Uniformity with Deckle Wave Control", Tappi Journal, Technical Association of The Pulp & Paper Industry, Atlanta, US, vol. 75, No. 7, Jul. 1992, pp. 121-128.
Pruitt, M., "How fourdrinier table control affects strength and speed on linerboard-Green Bay Packaging's Morriton, AR, mill" Nov. 30, 2008, available at: http://www.risiinfo.com/magazines/November/2008/PP/PPMagNovember-How-fourdrinier-table-control-affects-strength-and-speed-on-linerboard.html, last accessed Mar. 20, 2013.
IBS Paper Performance Group, Product Brochure, 2005.
Taiwanese first Office Action and Search Report for Application No. 110108000, dated Apr. 29, 2022, with English translation, 19 pgs.
M.H. Waller, On-line Papermaking Sensors: An Historical Perspective. In The science of papermaking, Trans. of the XIIth Fund. Res. Symp. Oxford, 2001, (C.F. Baker, ed.), pp. 785-895, FRC, Manchester, 2018. DOI: 10.15376/frc.2001.2.785.
V.V. Abramova, et al., Evaluation of Macrostructure Forming Uniformity of Copy Paper, UDC 676.017.27, DOI:10.17238/issn0536-1036.2017.4.172.
Russian Federation Office Action and Search Report for Application No. 2021105768, dated Jul. 28, 2021.

\* cited by examiner

FORMATION DETECTION SYSTEM AND A PROCESS OF CONTROLLING

CROSS-REFERENCE TO RELATED APPLICATION(S)

This application claims priority to and the benefit of U.S. Provisional Application Patent Ser. No. 62/986,239, filed Mar. 6, 2020, the entire disclosure of which is hereby incorporated by reference.

FIELD

The present teachings relate to a formation detection system that is connected to a control system for that monitors and controls formation along one or more sections of a paper machine and preferably an entire length of a paper machine.

BACKGROUND

Typically, fourdrinier paper machines include a wet end with a wire that moves in a machine direction. The wire has a width (i.e., cross-machine direction) and stock is applied substantially along the entire width of the wire. A plurality of blades are located under the wire and the plurality of blades assist in removing water from the stock on the wire. The blades are typically static, however, more recently foils and blades that actuate have been added to the wet end. Typically, changes to the paper machine are made by a user adjusting machine characteristics such as a slice opening or machine speed based upon dry end test results. Further changes to the paper machine may be made in the press sections, dryer sections, calender sections, or the reel. Each of these sections may introduce variability in the paper making process. Thus, there is a delay between testing dry end paper and making machine adjustments along of the paper machine, causing additional waste product, out of specification product, or increasing a duration of a grade change. Furthermore, most paper machines have one or two scanners, which are typically located proximate to the reel. If a change is made before the scanner, the scanner may detect the change; however, there is a lag and the precise location of the impact may not be known due to other variables changing continuously. Therefore, an operator may not know a precise location of section of the paper machine that is introducing some variability into the system.

Examples of monitoring and adjustment devices for paper machines are disclosed in U.S. Pat. Nos. 4,931,657; 6,129,817; 7,101,461; 7,695,592; and 8,325,225 all of which are expressly incorporated herein by reference for all purposes. Thus, there is a need for a device that monitors formation of each layer in a multi-layer sheet. What is needed is a device that monitors a final multi-layer sheet and is capable of extrapolating which layer has formation issues within the multi-layer sheet. What is needed is a monitoring system that monitors formation at a cut through. What is needed is a monitoring system monitors formation in, before, after, or a combination thereof a press section, a calender section, calender, reel, or a combination thereof. There is a need for a device that can track a point or line on a sheet of paper an entire length of a paper machine. What is needed is a monitoring system that monitors each stage of the paper machine so that the monitoring system assists in identifying which section is responsible for making a change to a sheet of paper (e.g., formation changes). What is needed is a real time system that assists in identifying a location of a negative change and assists in compensating for the negative change in real time.

SUMMARY

One possible embodiment of the present teachings provide: a formation detection system comprising: (a) one or more sensors and (b) one or more lights that illuminate a location of interest so that the one or more sensors can monitor the location of interest; wherein one of the one or more sensors are located substantially planar with a wire of a paper machine and proximate to a slice opening so that the one of the one or more sensors is adjacent to a cut through so that the one of the one or more sensors is capable of measuring stock above the wire and removed water below the wire, and wherein the one of the one or more sensors is capable of measuring a distance between an impingement location of a stock jet and the wire from a forming board.

The present teachings provide: a method comprising: (a) monitoring a wire proximate to a slice opening with one or more sensors so that a location above the wire is monitored and a location below the wire is monitored; (b) locating a location where a stock jet impinges with the wire; (c) locating a distal tip of a forming board or a distal tip of a first foil from the slice opening; and (d) measuring a distance between the location where the stock impinges with the wire and the distal tip of the forming board or the distal tip of the first foil.

The present teachings provide: a formation detection system comprising: (a) two or more sensors wherein the two or more sensors include: (i) a first of the two or more sensors is directed to a location along a paper machine corresponding to a first sheet of paper and (ii) a second of the two or more sensors is directed to a location along a paper machine corresponding to a second sheet of paper; (b) two or more lights; and (c) a control system; wherein formation of the first sheet of paper and formation of the second sheet of paper are matched up by the control system to form joint data so that when the first sheet of paper and the second sheet of paper are joined, formation data regarding the first sheet of paper and the second sheet of paper is recorded individually.

The present teachings provide: a method comprising: (a) monitoring formation of a first ply with a first sensor of a plurality of sensors; (b) monitoring formation of a second ply with a second sensor of the plurality of sensors; and (c) correlating the formation monitored by the first sensor with the formation monitored by the second sensor.

The present teachings provide: a formation detection system comprising: (a) one or more sensors and (b) one or more lights that illuminate a location of interest so that the one or more sensors can monitor the location of interest; wherein one of the one or more sensors are located within a press section of a paper machine, a dryer section, or both and the one or more lights monitor formation of a sheet of paper within the press section, the dryer section, or both.

A method comprising: a method comprising: (a) monitoring a sheet of paper with one or more sensors at one or more locations along a paper machine as the sheet of paper extends between two press rolls or two sets of press rolls of a press section or between two dryer cans a dryer section; (b) monitoring formation of the sheet of paper; and (c) monitoring surface characteristics of the sheet of paper.

The present teachings provide: a formation detection system comprising: (a) one or more sensors and (b) one or more lights that illuminate a location of interest so that the one or more sensors can monitor the location of interest; and wherein the one or more sensors are located within a calender section and monitor formation, surface characteristics, or both of a sheet of paper at one or more locations within the calender section.

The present teachings provide: a method comprising: (a) monitoring a sheet of paper with one or more sensors at one or more location along a paper machine as the sheet of paper extends into a calender section; (b) monitoring formation of the sheet of paper within the calender section; and (c) monitoring surface characteristics of the sheet of paper within the calender section.

The present teachings provide: a formation detection system comprising: (a) one or more sensors and (b) one or more lights that illuminate a location of interest so that the one or more sensors can monitor the location of interest; and wherein the one or more sensors are located within a reel section and monitor formation, surface characteristics, or both of a sheet of paper at one or more locations within the reel section.

The present teachings provide: a method comprising: (a) monitoring a sheet of paper with one or more sensors at one or more location along a paper machine as the sheet of paper extends into a reel section; (b) monitoring formation of the sheet of paper within the reel section; and (c) monitoring surface characteristics of the sheet of paper within the reel section.

The present teachings provide: a formation detection system comprising: (a) two or more sensors; (b) two or more lights that illuminate a location of interest, each of the two or more lights being located directly opposite one of the two or more sensors so that the one of the two or more sensors monitors the location of interest illuminated by each of the two or more lights; wherein a first of the two or more sensors is located in or after a wet end of a paper machine and a second of the two or more sensors is located in or before a press section of the paper machine.

The present teachings provide a device that monitors formation of each layer in a multi-layer sheet. The present teachings provide a device that monitors a final multi-layer sheet and is capable of extrapolating which layer has formation issues within the multi-layer sheet. The present teachings provide a monitoring system that monitors formation at a cut through. The present teachings provide a monitoring system monitors formation in, before, after, or a combination thereof a press section, a calender section, calender, reel, or a combination thereof. The present teachings provide a device that can track a point or line on a sheet of paper an entire length of a paper machine. The present teachings provide a monitoring system that monitors each stage of the paper machine so that the monitoring system assists in identifying which section is responsible for making a change to a sheet of paper (e.g., formation changes). The present teachings provide a real time system that assists in identifying a location of a negative change and assists in compensating for the negative change in real time.

BRIEF DESCRIPTION OF THE DRAWINGS

FIG. 4 is a side view of a cut through;

DETAILED DESCRIPTION

Figure 1:
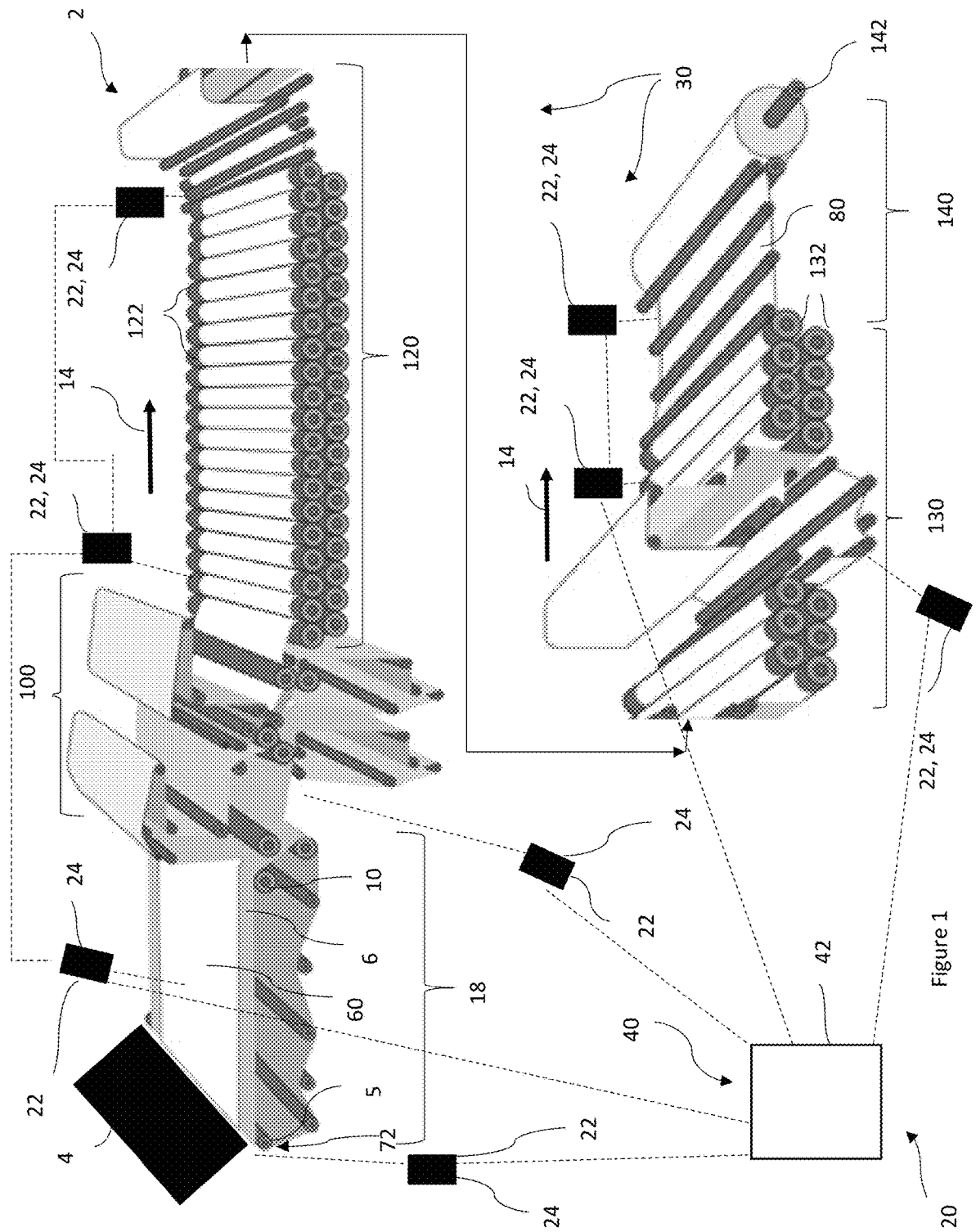
FIG. 1 is a side view of a paper machine including a formation detection system, a monitoring system, and a control system.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings are predicated upon providing an improved monitoring system, control system, method, or a combination thereof for monitoring and controlling formation of paper on a paper machine, and preferably a fourdrinier paper machine. The paper machine may be a gap former, a twin wire former, a cylinder machine, a saint ann's former, a counterflow vat, or a combination thereof. The paper machine may be any paper machine where stock traveling in a machine direction may be monitored and controlled. The paper machine taught herein may be any paper machine that functions to create paper. The paper machine may be any style and/or type that forms paper. The paper machine may have a single headbox or a plurality of headboxes. The paper machine may be a single ply paper machine. The paper machine may be multiple plies. The paper from the paper machine may have two or more, three or more, four or more, or even five or more plies. The paper from the paper machine may have 20 or less, 15 or less, or 10 or less plies. The paper machine includes a head box or vat that applies stock in a wet end.

The head box function to provide stock to a wire. The head box may be gravity fed, pressurized, static, or a combination thereof. The headbox may apply stock at a speed slower than the speed a wire in the wet end is moving (e.g., drag mode). The headbox may apply stock at a speed faster than the speed a wire in the wet end is moving (e.g., rush mode). The headbox may apply stock substantially at the same speed as the wire in the wet end is moving (e.g., square mode). The head box may function to apply stock to a wet end, above a breast roll, on foils, through a cut through, proximate to a forming board, above a forming board, or a combination thereof. The head box may function to apply stock to a wire while the wire passes over a forming board or over a forming section. The head box may apply stock to the wire at a location proximate to a breast roll and a forming board. The head box may have a variable slice opening. The slice opening may be variable in a cross-machine direction. For example, one edge may be varied and adjacent portion may be static. The head box may have a static slice opening. The slice opening may be pressure controlled. The pressure may be varied along a cross-machine direction of the paper machine. The head box may have a top portion that is movable up and down. For example, a static head of fluid may be adjusted by moving a top of the head box up or down, or the amount of stock applied to the wire may be adjusted by moving a top of the head box up or down (e.g., adjusting a slice opening. The head box may include one or more slice openings.

The slice opening may function to guide stock from the head box onto the wire. The slice opening may vary a velocity of stock traveling onto a wire, a volume of stock onto a wire, an angle of stock approaching a wire, or a combination thereof. The slice opening may be adjusted. The slice opening may have a top portion or a bottom portion that are movable. The top portion may increase a height or decrease a height of a slice opening. The top portion may pivot so as to change an angle of the stock jet while increasing a distance between the top portion and the bottom portion. The bottom portion may be movable in the machine direction. The bottom portion may change a distance between the head box and the forming board. The bottom portion, the top portion, or both may change an angle of the stock jet relative to the wire, the forming board, or both. The top portion, the bottom portion, or both may move in the machine direction (e.g., forward and backward); up and down (e.g., towards and away from the wire; pivot a portion towards or away from the wire; or a combination thereof. The slice opening may be a fixed slice opening. The stock passed through the slice opening may be controlled by controlling a pressure differential along a cross-machine of the paper machine. For example, the pressure applied to the stock may var along the paper machine in increments. The increments may be 1 mm or more, 5 mm or more, 1 cm or more, 3 cm or more, or 5 cm or more. The increments may be 50 cm or less, 25 cm or less, or 10 cm or less. The slice opening may affect a contact location, contact angle, stock velocity, or a combination thereof of the stock jet relative to the wire, breast roll, forming board, forming section, or a combination thereof.

The stock jet functions to place stock on a wire while beginning to impart certain characteristics into the fibers in the stock. For example, if a stock jet is moving slower than a wire (e.g., drag) the fibers may tend to be aligned in the machine direction. In another example, if the stock jet is moving at a same speed as the wire the fibers may tend to be more randomly oriented than when the stock jet is in rush or drag. The stock jet may affect formation of paper. The stock jet may be substantially parallel to the wire. The stock jet may impinge into the wire. The stock jet may extend out of the slice opening at an angle of about 1 degree or more, about 3 degrees or more, about 5 degrees or more, about 7 degrees or more, or about 10 degrees or more relative to a plane parallel to the wire so that the stock jet is angled towards the wire. The stock jet may extend out of the slice opening at an angle of about 45 degrees or less, about 30 degrees or less, or about 15 degrees or less relative to a plane parallel to the wire so that the stock jet is angled towards the wire. The stock jet may first hit a bottom of the slice opening before being transferred to the wire. The stock jet may come out of the slice opening and first contact the wire above the breast roll or the forming board. The stock jet may exit the slice opening and hit the wire between the breast roll and the forming board or forming section. The angle, contact location, speed, velocity, or a combination thereof may be controlled depending on measured activity on the wire of the paper machine. The stock jet may impinge with or contact a wire at a cut through or a location proximate to a cut through. Depending on the angle, speed, consistency, contact location, or a combination thereof the stock may begin to be dewatered by the wire by water being forced through the wire.

The wire may be a porous continuous belt that travels between the breast roll and the couch roll and carries stock. The wire may be flexible enough to be moved and changed by the foils within the various foil sections. The wire may be made of or include metal, plastic, a polymer, woven, nonwoven, or a combination thereof. The wire may include pores so that water may be removed from the stock but solids retained. The wet end may have a wire that travels in a machine direction with stock and the stock is dewatered as the wire moves in the machine direction. Preferably, the wet end includes an endless wire that travels in a machine direction. The width of the wire may extend in the cross-machine direction. The wet end may have opposing edges that may have stock that runs along a cross-machine direction and falls off the wire. The wet end may end with a couch roll (i.e., couch roll end) that functions to wrap the wire and guide the wire in a direction opposite the machine direction so that an endless wire is formed. The couch roll may function to dewater. The couch roll may include suction. The couch roll may end the wet end. The couch roll may assist in guiding a sheet from the wet end into a press section. The stock may be sufficiently dry when the stock reaches the couch roll that the stock has paper like qualities and is self-supporting. The stock may be sufficiently self-supporting once a dry line is visible in the stock. The dry line may be monitored by a monitoring system. The wire may carry stock from the head box to a press section.

Stock as discussed herein is a slurry of fibers mixed in water and optional paper chemicals to enhance certain final paper characteristics. Stock may include fiber, fines, fillers, chemicals, virgin fibers, recycled fibers, synthetic fibers, mineral fibers, glass fibers, polymer fibers, or a combination thereof. Stock as discussed herein may be a sheet of paper once move out of the head box despite being primarily water. The stock preferably is at 90 percent or more, 95 percent or more, or even 99 percent or more water at the headbox (e.g., has a consistency of about 1 percent or less stock and 99 percent or more water by weight). As the stock travels in the machine direction (i.e., a direction of movement from a wet end to a dry end) the foils or blades and groups of foils (e.g., foil sections) or groups of blades (e.g., blade sections) remove the water and consistency (i.e., percentage of water in the stock) decreases (stated another way the weight percentage of fibers increases as the sheet moved in the machine direction). Water may continually be removed from the stock as the stock travels toward the wet end. The stock at some point will go from being a primarily liquid state to being a primarily solid state, which is referred to a dry line (i.e., a visible point on the paper machine where the stock goes from dark to light (typically at a sheet consistency of between about 8 percent to about 10 percent)).

The dry line functions to indicate that a sheet is formed and the sheet is becoming solid. The water may be removed to a point where a "dry line" is visible. The dry line is a line that forms in the cross-machine direction (i.e., a direction 90 degrees to the machine direction) where a sufficient amount of water is removed so that the stock no longer appears glossy or wet. The dry line may be substantially straight. The dry line may be staggered and the dry line may appear at edges of the paper machine before the dry line appears in a center of the paper machine. For example, the dry line may appear to have one or more fingers. The dry line may be monitored by one or more sensors. The size, shape, location, distance from the head box, or a combination thereof of the dry line may be controlled. Formation at the dry line may be monitored by one or more sensors. Formation before the dry line and formation after the dry line may be monitored to monitor any changes in formation. The one or more sensors may monitor a contrast from a wet side to a dry side of the dry line. The one or more sensors may monitor a width of a transition zone from a wet side to a dry side of the dry line. The one or more sensors may monitor a shape of the dry line, a length of fingers extending form the dry line, a histogram of movement of regions or fingers of the dry line, or a combination thereof. The dry line may be controlled, changes, or adjusted by turning on, turning off, reducing fluid, or a combination thereof formation showers. The formation showers may be controlled based upon sensors sensing formation at the dry line.

The sensors taught herein function to monitor the formation, defects, or both of the sheet at one or more and plurality a plurality of locations along a paper machine. The formation may be the orientation of the fibers, spacing between fibers, a lack of fibers, elevated fibers, topography of the fibers, spaces between fibers, flocks of fibers, or a combination thereof. For example, the formation may be measured by changes in opacity or differences in opacity between sub-regions within a region of a sheet. The changes in opacity may be due to concentrations of fibers in some sub-regions and a lack of concentrations in other sub-locations (e.g., light spots v. dark spots). For example, the sensors may monitor a region (e.g., 1 m by 1 m) and the region may be broken up in to a plurality of sub-regions (e.g., 1 cm by 1 cm) and each of the sub-regions may be compared to one another to determine changes in opacity or formation. The changes in the opacity or formation may then provide a numerical formation representation. The formation may be a number of flocculations per area, the size of the flocculations, flocculations on a surface of a sheet, or a combination thereof. Formation may be a measurement of uniformity of a sheet with respect to fiber distribution. The formation may be based upon a visual characteristic. The uniformity may be based upon an amount of mottle as a measure of a visual characteristic. The less mottle of the sheet the better the formation may be. The more mottle to the sheet the poorer the formation may be. The measure of uniformity may be based upon a grey scale that translates opacity or a uniformity of the grey scale in an area. For example, if all of the images taken have a consistent color without light spots or dark spots then formation may have a low numerical value and be considered good (e.g., the numerical formation representation may be closer to 1). If the images have a large number of light spots, darks spots, or both then the formation may have a high numerical value and formation may be considered to be poor (e.g., the numerical formation representation may be closer to 100). Formation may be monitored before the dry line by monitoring activity of the stock; however, the dry line may be a first location where formation of a sheet may be tracked as at the dryline the fibers are no longer suspended in fluid. The dry line is located between the breast roll and the couch roll. The dry line may occur after a wet line (i.e., downstream in the machine direction).

The wet line may function to indicate a location on the paper machine where a sufficient amount of water is removed so that the stock no longer reflects light or has a mirrored appearance, fibers cease to move, or both. The wet line may occur at a consistency of between about 5 percent and about 6 percent (i.e., about 5 percent solids and 95 percent water by weight). The wet line may indicate that sheet formation has occurred. Formation of the fibers may be monitored before the wet line, after the wet lines, at the wet line, or a combination thereof. The wet line may indicate that the fibers are substantially immobilized (e.g., there is not a sufficient amount of fluid that the fibers are still suspended within the fluid and freely move). The wet line may indicate that the sheet has transitioned from primarily a liquid to a solid or a semi-solid. The wet line may occur after the stock activity line.

The breast roll may be the first roll of the wet end (i.e., at the head box end), may assist in formation, may remove water from the stock, or a combination thereof. The breast roll may be the lead roll in a wet end. The breast roll may be located on an opposite end of the wet end as the couch roll in the machine direction. The couch roll may be a last roll on the wet end of the paper machine. The couch roll may be located between the wet end and the press sections. The wet end may function to receive stock and dewater stock. One or more forming boards, forming sections, or both may be located between the breast roll and the foil sections.

A forming section may be located downstream of the breast roll. The forming section may function to assist in receiving stock from the slice opening and to assist in configuring the stock so that fibers in the stock are oriented in a desired orientation (e.g., machine direction, cross machine direction, random, square). The forming section may include one or more foils, one or more forming boards, or both. The first foil of all of the foil sections may be a forming board. The forming board may be static. The forming board may be movable in the machine direction.

The forming board may move so that the distance between the forming board and the head box and/or head box slice opening is increased or decreased. The forming board may be height adjustable. The forming board may be angle adjustable. The forming board may be moved to increase or decrease the amount of water removed from the stock jet.

The wet end may be a portion of the paper machine where the paper has a consistency of about 15 percent or less or about 10 percent or less. The wet end may be a portion of the paper machine that is located upstream of a press section. The wet end may receive stock that is primarily water and remove the water until a sheet is formed. The wet end may have one or more and preferably a plurality of foil sections (or blade sections). For example, the wet end may have a first section, second section, third section, fourth section, or more. The wet end may remove water from stock. The wet end may impart activity into the stock so that formation of the stock is controlled, formation of a sheet of paper is controlled, the fibers are oriented or reoriented, the fibers remain suspended within water. The wet end may include one or more activity showers.

The one or more activity showers may function to introduce turbulence, activity, water, chemicals, or a combination thereof into the wet end. The one or more activity showers, may be located in or over a first section, a second section, a third section, a fourth section, or a combination thereof. The one or more activity showers may add water, spray water, or create turbulence within the stock that has been placed on the wire so that the stock may be dewatered, reoriented, maintained in solution, or a combination thereof. The one or more activity showers may break-up fibers on the wire. The one or more activity showers may spray a fluid, jet a fluid, drop a fluid, or a combination thereof into the stock or unto the wire. The one or more activity showers may be selectively applied. For example, if poor formation is monitored then the activity showers may be activated to change the formation. The activity showers may be applied across a portion of the cross-machine direction, for a duration along the machine direction, or both. The activity shower may be controlled by the control system, the monitoring system, or both. The sheet may be monitored before the activity showers, after the activity showers, or both. The amount of change from the activity showers may be ascertained from before the activity shower and after the activity shower. For example, a formation number may be ascertained before the activity shower and a formation number may be ascertained after the activity shower and the change in formation may be calculated (e.g., delta). The change in formation may be determined using the monitoring system to determine if the activity showers are improving formation. The change in formation may result in the controller turning off, turning on, or adjusting the activity showers. The activity shower may be controlled by changing pressure of the fluid coming out of the activity shower (e.g., increasing or decreasing); changing a volume of fluid coming out of the activity shower (e.g., increasing or decreasing); changing temperature of the fluid; varying an angle and/or height of the fluid coming out of the activity shower relative to the stock; or a combination thereof. If activity is not within a predetermined parameter then the activity shower may be turned on, turned off, increased, decreased, or some condition therebetween to change the activity within the wet end. The wet end may have a plurality of sections of foils or blades.

The first section may function to begin dewatering stock as the stock exits the head box, the slice opening, the forming board, the forming board section, or a combination thereof. The first section may include static foils, height adjustable foils, angle adjustable foils, or a combination thereof. The various foils may be alternating; only static; all height adjustable foils; all angle adjustable foils; height adjustable foils and angle adjustable foils; height adjustable foils and static foils; angle adjustable foils, height adjustable foils, and static foils; or a combination thereof. Preferably, the first section is a combination of angle adjustable foils and height adjustable foils; all height adjustable foils; or all angle adjustable foils. The first section may be vacuum assisted. The first section may be free of vacuum assistance. The first section may maintain formation of the fibers or orientation of the fibers coming out the headbox. The first section may assist in the paper in fiber formation. The first section may be located directly upstream of the second section.

The second section may function to continue dewatering stock as the stock travels in the machine direction. The second section may dewater stock that is exiting the first section. The second section may include static foils, height adjustable foils, angle adjustable foils, or a combination thereof. The various foils may be alternating; only static; all height adjustable foils; all angle adjustable foils; height adjustable foils and angle adjustable foils; height adjustable foils and static foils; angle adjustable foils, height adjustable foils and static foils; or a combination thereof. Preferably, the second section is a combination of static foils and height adjustable foils with vacuum assist. The second section may be vacuum assisted. The second section may be free of vacuum assistance. The second section may maintain formation of the fibers or orientation of the fibers coming out the headbox. The second section may assist in the paper in fiber formation. The second section may be located directly upstream of the third section.

The third section may function to continue dewatering stock as the stock travels in the machine direction. The third section may dewater stock that is exiting the second section. The third section may include static foils, height adjustable foils, angle adjustable foils, or a combination thereof. The various foils may be alternating between different types of foils; only static; all height adjustable foils; all angle adjustable foils; height adjustable foils and angle adjustable foils; height adjustable foils and static foils; angle adjustable foils, height adjustable foils, and static foils; or a combination thereof. Preferably, the third section is a combination of static foils on ends and angle adjustable foils located therebetween with the third section including vacuum assist. The third section may be vacuum assisted. The third section may be free of vacuum assistance. The third section may maintain formation of the fibers or orientation of the fibers coming out the headbox. The third section may assist in the paper in fiber formation. The third section may be followed by a fourth section, a vacuum section, steam boxes, a high vacuum section, or a combination thereof that may include blades or foils. The control section may include one or more sensors that may be located within the first section, the second section, the third section, or a combination thereof.

Blades and foils as discussed herein may be used interchangeably. The foil sections may each include one or more foils and preferably a plurality of foils. The foils may be height adjustable, angle adjustable, fixed, or a combination thereof. The foil sections may include one or more forming boards. The forming boards may be part of a forming board section. The forming board may be a first board on a paper machine. The forming board may be movable in the machine direction, cross-machine direction, or both. The forming board section may include height adjustable foils, angle adjustable foils, fixed foils, static foils, or a combination thereof. The foils and blades may be adjusted by any device as taught herein including devices taught in U.S. Pat. No. 8,551,293 in column no. 3, line 30 through column no. 10, and FIGS. 1-9B the teachings of which are expressly incorporated by reference herein regarding angle and height adjustable foil or blades. The foils or blades may be adjusted in angle and/or height as taught herein including devices taught in U.S. Pat. No. 9,045,859 in column 1, line 50 through Column 16, line 24 and FIGS. 1-9B the teachings of which are expressly incorporated by reference herein regarding angle and height adjustable foil blades including cam blocks, grooves, guide keys, connecting rods, thrust end blocks, pivots, foils, pneumatic, hydraulic, bending structure or a combination thereof. The wet end includes edges in a cross-machine direction (i.e., a direction that is perpendicular to a machine direction). The plurality of foils may be broken into one or more groups of foils and preferably a plurality of groups of foils that extend in the machine direction. The groups of foils may be all height adjustable, all angle adjustable, all static, or a combination thereof. The groups of foils may include both height adjustable foils and angle adjustable foils; both static and height adjustable, both static and angle adjustable; height adjustable foils, angle adjustable foils, and static adjustable foils; or a combination thereof. The types of blades may be alternating (e.g., static blades and height adjustable blades; static and angle adjustable blades; height adjustable blades and angle adjustable blades; or a combination thereof). The static blades may be located at a beginning and an end and angle adjustable or height adjustable blades may be located therebetween. The paper machine may include two or more groups of foils, three or more groups of foils, four or more groups of foils, or five or more groups of foils. Each group of foils may include two or more foils, four or more foils, six or more foils, or even ten or more foils. A first set of foils may include a forming board and then a set of foils. The types of foils (e.g., static, angle adjustable, height adjustable) may be grouped in any order. For example, the group of foils may include two angle adjustable foils then one static foil and the three height adjustable foils. Each foil may be a different type in an alternating fashion. For example, a static foil then height adjustable in a repeating pattern. The height adjustable foils may move a distance from a wire (e.g., out of contact with the wire). The height adjustable foils may move towards or away from the wire. The height adjustable foils may from away from the foil about ±1 mm or more, about ±2 mm or more, about +3 mm or more, about ±4 mm or more, about ±5 mm or more, or about ±6 mm or more (e.g., when the foil moves towards the wire it is positive (or up) and when the foil moves away from the wire it is negative (or down)). When the height adjustable blades are in contact with the wire and the wire is not deflected then the height adjustable blades are at 0 mm. The angle adjustable blades may be adjustable in an angle from about ±1° or more, about ±2° or more, about ±3° or more, or about ±4° or more (e.g., when a tip of the blade is rotated into the wire (i.e., up pressing into the wire) the angle is positive and when the tip of the blade is rotated away from the wire (i.e., down moving away from the wire) the angle is negative, and when the tip is parallel to the wire the angle is 0°). The height adjustable foils may create vacuum on the wire that pulls the wire negative. The height adjustable foils may have a "v" shape and the valley of the "v" may assist in pulling the wire below 0° so that stock activity is created. The blades may be adjusted based upon one or more monitored conditions of a monitoring system. Preferably, a monitoring system monitors the stock at one or more locations between the headbox and the reel. The monitoring system may monitor formation leaving the wet end and extending into a press section.

The press section functions to dewater the sheet. The press section functions to gradually increase solids at a low cost. The press section may have one or more presses (or nips), two or more presses, three or more presses, five or more presses, or seven or more presses. The press section may have 20 or less presses or 15 or less presses. Each of the presses may be two rolls located opposite one another forming a nip that the sheet extends through so that water is removed. The presses may have a nip that applies pressure to remove water. The presses may apply a load to the sheet. The presses may gradually increase an amount of pressure on the sheet to dry the paper. The presses may have a drainage box so that an amount of water removed may be monitored. The rolls may be covered by felt that absorbs the water and then the water may be removed from the felt by a vacuum that may be monitored. The hardness of the presses may affect an amount of water removed from the sheet. The presses may be loaded to a pressure depending on material characteristics of the roll, draining characteristics of the sheet, or both. The monitoring system may monitor before each nip, after each nip, before the press section, after the press section, in a center of the press section, or a combination thereof (e.g., may include a sensor in those locations). A numerical value (e.g., numerical formation representation) may be assigned at each location so that the monitoring system may monitor for formation changes. For example, if too much pressure is applied the sheet may be crushed, water may be removed too quickly and cause the fibers to flow, or both, which may cause a change (e.g., delta) in formation. The press section may be monitored so that a pre-determined amount of water is removed. The press section may have pressure increased, pressure decreased, indicate a different hardness is needed, vacuum needs to be changed, the machine needs to be slowed down, or a combination thereof depending upon the delta in formation measured. The monitoring system may monitor a sheet coming out of the press section and extending into the dryer section.

The dryer section functions to remove water from the sheet. The dryer section may have one or more zones, two or more zones, three or more zones, four or more zones, or five or more zones. The dryer section may have twenty or less zones, fifteen or less zones, or ten or less zones. The zones may gradually increase in temperature or pressure. The monitoring system may include one or more sensors located before each zone, after each zone, before the dryer section, after the dryer section, or a combination thereof. The formation affected within the dryer section may be monitored so that changes in formation may be tracked. For example, if a dryer can is moving at a different speed than the other dryer cans (or another dryer can section) or a dryer felt the sheet be damaged by the dryer can or the dryer felt pulling on the sheet. This damage may be observed through a delta in formation. In another example, tension may change from dryer can to dryer can or section to section and this change in tension may cause drag on a dryer can that may impact formation. The sheet exiting the dryer section may be monitored before entering the calender section.

The calender section functions to smooth a sheet, densify a sheet, or both. The calender section may include one or more nips, two or more nips, three or more nips, or four or more nips. The calender section may include 10 or less nips, 7 or less nips, or 5 or less nips. The calender section may include two or more calender sets each including a plurality of nips. The sheet may be monitored entering a nip, exiting a nip, entering a calender set, exiting a calender set, or a combination thereof. The monitoring system may include one or more sensors at each of the nips monitoring formation, the sheet extending through the nip, or both. If the delta in formation changes then pressure of the calender may be changed (e.g., increased or decreased), the number of nips may be reduced, the number of nips may be increased, water may be added, water may be removed, or a combination thereof. The monitoring system may monitor the calender section for formation changes (e.g., crushing of the paper causing light spots in regions where the sheet is crushed and dark spots in regions where the fibers are forced by the crushing. The monitoring system may monitor the sheet exiting the calender or entering the reel.

The monitoring system may function to monitor formation of fibers within a wet end, press section, calender section, dryer section, between sections, within the wet end, between press nips, between dryer rolls, between calender rolls, before a scanner, after a scanner, before a water box, after a water box, before combination with other plies, after combination with other plies, or a combination thereof of a paper machine. The monitoring system may monitor in the cross-machine direction, the machine direction, or a combination of both. The monitoring system may monitor substantially normal to the sheet. For example, a light may be located on a first side of the sheet and the sensor may be located on a second side of the sheet. The sensor may monitor at an angle of about 60 degrees or more, about 75 degrees or more, about 85 degrees or more, about 90 degrees, or about 105 degrees or less relative to the sheet. The monitoring system may monitor activity, amplitude, size, scale, duration of activity, formation, or a combination thereof in a cross-machine direction, a machine direction, substantially normal to the sheet, in a region, or a combination of both. The monitoring system may measure stock activity, amplitude, size, scale, duration of activity, formation, or a combination thereof (hereinafter all will be referred to as stock movement). The monitoring system may monitor stock activity, analyze stock activity, relay information regarding stock activity to a control system, monitor formation, monitor changes in formation, or a combination thereof in real time. The monitoring system may monitor the amount of water removed by one or more of the foils; the forming board; the impingement angle between the stock jet and the wire; height or angle of the forming board; nips; press rolls, dryer cans; dryer sections; calender nips; calender sections; each stock section; or a combination thereof. The monitoring system may monitor the cut through near the head box. The monitoring system may be located at, alongside, perpendicular to, or a combination thereof a cut through on the paper machine (e.g., be coplanar with the cut-through and aimed in a cross-machine direction).

The cut through may be the area between the slice opening and the forming board, between the head box and the forming board, between the breast roll and the forming board, or a combination thereof. The monitoring system may monitor the width of the water being removed. The amount of water removed may be calculated be monitoring a width of the water and the machine speed. A flow meter may measure an amount of fluid being removed. The monitoring system may monitor the impingement angle between the stock jet and the forming board. The monitoring system may monitor the amount of water removed by adjusting a gap between the forming board and the head box, an angle of one or more blades, a height of one or more blades, or a combination thereof. The monitoring system may monitor the location of the bottom portion of the head box relative to the breast roll, the forming board, or both. The monitoring system may include one or more lights, one or more sensors, one or more level devices, or a combination thereof. The monitoring system may monitor the activity line, the stock activity line, a wet line, dry line, or a combination thereof. Preferably, the monitoring system includes a plurality of sensors that monitor the wet end of the paper machine.

The one or more sensors function to monitor the stock activity (i.e., movement), sheet formation (e.g., a relationship of the fibers and voids within a sheet), a change in formation due to stock activity, a change in formation due to a section of the paper machine, or a combination thereof. The sensors may function to indicate a location where a formation delta occurs. The one or more sensors may function to send signals to a control system so that the control system controls the stock movement, formation, or both. The one or more sensors function to monitor and assist in controlling stock movement (i.e., activity) in real time so that final paper quality (e.g., formation) may be changed without waiting for testing results from a dry end of a paper machine. The one or more sensors may assist in making adjustments during a grade change, normal running, or both. The one or more sensors may monitor a temperature of the stock or sheet. The one or more sensors may monitor a first side and a second side of the stock activity line, the wet line, the dry line, or a combination thereof. The one or more sensors may monitor a temperature profile, a humidity profile, a dryness profile, or a combination thereof. The one or more sensors may monitor the stock jet. The one or more sensors may monitor jet impingement of the stock jet relative to the slice opening, the wire, the forming board, the forming board section, or a combination thereof. The one or more sensors may monitor a location proximate to a steam box. The one or more sensors may monitor for streaks, temperature profile, dryness profile, light spots, dark spots, or a combination thereof. The sensors may monitor stock movement and correlate the stock movement to a previous run and then provide signals to the control system to adjust the paper machine to match the activity (e.g., stock movement) of the previous run. The sensors may measure an amount of water removed by a uhle box, a press roll, a press section, a shoe press, a steam shower, a vacuum section, or a vacuum roll, or a combination thereof.

The sensors may be a camera that takes still images, moving images, or both. The sensors may use ultrasound, infrared, CMOS sensor, charge-coupled device, matrix camera, area scan camera, line scan camera, microwave, a temperature sensor, nuclear, capacitance, pressure, vacuum, distance, suspension height, a flow sensor, flow meter, level sensor, a volume sensor, or a combination thereof. The one or more sensors may be a plurality of sensors or a multitude of sensors. All of the sensors may be the same type of sensor. Different types of sensors may be used together. For example, one sensor may be an infrared sensor and another sensor may be a CMOS sensor. The one or more sensors may be a color sensor that senses a color of the sheet within a greyscale spectrum (e.g., intensity). The one or more sensors may be monochrome sensor. The one or more sensors may monitor a dry line without use of cameras (i.e., dry line monitoring may be done without lights). The one or more sensors may be one or more sensors, two or more sensors, four or more sensors, six or more sensors, ten or more sensors, or even twenty or more sensors.

Each of the sensors may produce images that have a plurality of pixels or a plurality of sub-regions. Each of the sensors may produce pixels or sub-regions that may be categorized. The pixels or sub-regions of the sensors may be categorized based upon a primary activity, secondary activity, tertiary activity, or more activities (e.g., 4 groups, 5 groups, 6 groups, or more). The pixels or sub-regions may be categorized by lightness and darkness. For example, a grey scale may be monitored from white to black and the pixels or sub-regions may be categorized according to where each pixel or sub-region fits on the greyscale. The pixels may be categorized on a size or intensity of a light region or light spot or a size or intensity of a dark region or dark spot. For example, the greyscale may have a range from 0 (e.g., black) to 255 (e.g., white) and every integer or fraction of integer there between. The greyscale may be calculated by an intensity of light in each pixel or sub-region. For example, if no sheet is present and a light shines directly into the sensor an intensity or greyscale measurement of 255 may be measured. If a sheet completely blocks the light then the intensity or greyscale measurement may 0. Thus, the more uniform the intensity of light is the better the formation is considered. If a sheet is free of light spots and dark spots the sheet may have better formation characteristics then a sheet that includes a high number of light spots and dark spots. The size, area, intensity, or a combination thereof are measured to determine formation in each region, pixel, sub-region, or a combination thereof. Each image may be broken down into a predefined number of pixels or sub-regions and then each pixel or sub-region may be scored with a number. The numbers may be calculated and then a difference between the high and the low number may be used to determine the formation. For example, if the lowest number is a 30 and the highest number is a 40 then the formation may be a 10 (i.e., good formation). In another example, if the lowest number is a 40 and the highest number is a 100 then the formation may be a 60. The formation may be determined based upon a difference from an average and a high number or a lower number. Outliers may be removed in determining the numerical formation representation. A difference between a high and low of each digit may represent a formation number of about 0.25 or more, about 0.5 or more, about 0.75 or more, or about 1. A difference between a high and low of each digit may represent a formation number of about 5 or less, about 3 or less, or about 2 or less. For example, every 1 point of difference between the high and low number may result in a formation change of about 0.4. Thus, a grey range of 30 to 70 may result in a formation number of about 15.6. If a change was made and the sheet began to get crushed and the delta changed from 40 to 70 the formation number would change from 15.6 to 27.3 resulting in a formation delta of 11.7. This delta indicates that whatever change is being made is making the formation worse and may indicate that final sheet properties at the dry end will likely decrease. Thus, the monitoring system may trigger a reversion of a change made to compensate for the delta in formation. For example, if loading was increased on a press and then the delta in formation jumps the monitoring system may automatically undue the loading increase or may trigger an alarm to alert an operator that the change made has negative implications on formation. The activity settings or formation settings may be from a group or predetermined settings that a user may control.

The groups of activity or formation may be selected based upon one or more predetermined activity settings or formation settings. The groups of activities may be compared to one or more threshold activities. The one or more threshold activities may separate the activities into a primary, secondary, tertiary, etc. . . . . The primary activity, secondary activity, and tertiary activity may be measured by one or more sensors. The formation or formation settings may be measured relative to a control for a specific grade. For example, a 30 point grade may be more opaque than a 20 point grade and thus the differences in opacity may be less apparent and a multiplier used to calculate a delta may have to be greater. For example, a 20 point sheet may have a maximum whiteness of about 230 and a 30 point sheet may have a maximum whiteness of about 200 due to the additional thickness. Thus, a multiplier may change from grade to grade or for each of the caliper types or thicknesses. The multiplier may assist in calibrating the formation from grade to grade. The multiplier may be the same from sensor to sensor.

The one or more sensors may include an air purge. The one or more sensors may include a cleaning mechanism. The one or more sensors may include a self-cleaning lens. The one or more sensors may include a wipeable lens. For example, the wipeable lens may be a self-wiping lens that upon a pre-determined amount of build-up moves so that the debris is removed from the lens. The lens may move longitudinally or radially so that a cleaned lens is moved in front of the camera. The one or more sensors may include both a cleaning mechanism and an air purge. The one or more sensors may remove vapor, fluids, steam, debris, stock, or a combination thereof. The one or more sensors may be in a location so that the sensors are a high angle sensor, a low angle sensor, a movable sensor, or a combination thereof.

The one or more movable sensors may be located above the wet end and the one or more movable sensors may move in the machine direction, the cross-machine direction, or a direction therebetween. The movable sensors may function to travel along a wire. The movable sensors may travel with an area of stock. For example, the sensor may match the speed of the wire and take readings of the changes occurring to a location on the wire to determine the impact of each foil, section, press, calender, dryer, steam shower, water box, or a combination thereof on activity, formation, or both. The movable sensors may move along the stock activity line, the wet line, the dry line, or a combination thereof. The movable sensors may be connected on a frame, a wire, may be a drone, may be free of connection with any devices, may be suspended from a ceiling, may be suspended over the head box and movable along the head box, or a combination thereof. The movable sensors may zoom in, zoom out, or both. The movable sensors may be movable with a light so that an area of interest is illuminated while the movable sensor moves. The movable sensors may move diagonally. For example, the movable sensor may move in the machine direction as the movable sensor scans in the cross-machine direction so that the movable sensor measures in a straight line across the sheet. The movable sensors may be a plurality of sensors. The movable sensors may be a camera, a thermal camera, a temperature sensor, or a combination thereof. There may be multiple movable sensors that move over the wet end to allow a user to monitor one or more locations of the wet end simultaneously. The movable sensors may be wired, wireless, use Bluetooth, use wifi, use radio waves, or a combination thereof. The movable sensors may be in communication with other sensors and may move to a location of interest based upon measurements taken by other sensors. The movable sensors and other sensors may be in communication with the control system and the control system may control where the movable sensor senses based upon feedback detected by the sensors (e.g., the high angle sensors, the low angle sensors, or both).

The one or more high angle sensors may function to be located above the sheet and look substantially down at the sheet to monitor the sheet of the paper machine. The one or more high angle sensors may be substantially normal (e.g., 90 degrees) to the sheet regardless of the angle of the sheet. For example, if the sheet is extending vertically through a dryer section the high angle sensor may be facing parallel to a floor so that a high angle is maintained (e.g., normal position). In contrast, a low angle sensor may be located substantially coplanar or at a low angle (e.g., 15 degrees or less) relative to a sheet. The high angle sensors may be located substantially overhead of the wet end, the press section, the dryer section, the calender section, the reel, or a combination thereof. The high angle sensors may be orthogonal to the wire, the wet end, a sheet, a felt, a press, a dryer, a calender, a reel, any location therebetween, or a combination thereof. The one or more high angle sensors may monitor a stock activity line, a wet line, a dry line, or a combination thereof. A plurality of high angle sensors may be located in the cross-machine direction across the paper machine so that a cross-machine profile or formation may be created. The high angle sensors may each monitor a portion of a width (i.e., cross-machine direction) of the paper machine. The high angle sensors may monitor overlapping regions. The high angle sensors may be located in a line along the machine direction so that the sheet is continuously monitored as the sheet travels along the paper machine. The high angle sensors may be located about 90 degrees or less, about 75 degrees or less, about 60 degrees or less, or about 45 degrees or more with the wet end, wire, foil sections, dryer, press, calender, reel, a sheet, a location therebetween or a combination thereof. The high angle sensors may monitor the stock movement, formation within the sheet, or both. Preferably, the high angle sensors monitor activity, size, scale, amplitude of the stock, formation of the sheet, or a combination thereof. The high angle sensors may work in conjunction with or separately from the one or more low angle sensors.

The one or more low angle sensors may function to measure stock movement, dewatering, formation, or a combination thereof. The one or more low angle sensors preferably monitor stock amplitude and/or stock activity. The one or more low angle sensors may be substantially coplanar with the wire, the foils, the wet end, or a combination thereof. The one or more low angle sensors may be angled parallel to the cross-machine direction, perpendicular to the machine direction, or both. The one or more low angle sensors may be located a sufficient height above a deckle board to monitor stock movement on the wire, the foils, the wet end, the dry end, a press section, a dryer section, a calender section, the reel, a location therebetween, or a combination thereof. The one or more low angle sensors may have an angle of about 0 degrees or more, about 5 degrees or more, about 15 degrees or more, about 25 degrees or more, or about 45 degrees or less relative to the wire, the foils, the wet end, a sheet, a felt, or a combination thereof. The one or more sensors (e.g., high angle, moving, low angle, or a combination thereof) may monitor the amount of activity of the stock or formation within a given region. For example, the sensors may count the total number of peaks (i.e., spouts that extend from the wire, which are shown in the figures as light spots or stock jumping up from the wire) formed in the stock that extend above a predetermined point (e.g., a level device or activity line). The sensor may monitor the amount of the fluid (e.g., water) being removed by each foil, a uhle box, a press roll, or a combination thereof. For example, if one foil or press roll is removing too much fluid then the stock activity may be changed so that less may be taken out in the location or more may be removed before that section. In another example, if enough fluid is not removed from a foil, group of foils, press rolls, uhle box, or a combination thereof then a sufficient dryness may not be achieved. The one or more low angle sensors may monitor each foil or foil section so that substantially the same out of fluid is removed by each foil or foil section. The one or more low angle sensors may monitor the amplitude of the stock, formation of a sheet, or both. For example, the low angle sensors measure a height the stock is agitated above the wire, the foils, a level device, an activity line, or a combination thereof.

The one or more lights may function to illuminate the stock movement so that the stock movement can be measured, sheet formation, or both. The one or more lights may be part of the monitoring system. The one or more lights may freeze the stock so that the stock activity, formation, or both are visible. For example, the lights may be a strobe light. The lights may be connected to a monitoring system that may control the frequency of the lights turning on and off, the strobing of the lights, or both. The one or more lights may be connected to each of the sensors or located opposite a sensor. Preferably, the monitoring system includes a plurality of sensors. Some of the lights may be located on a back side or under side of a sheet. Some of the lights may be located on an opposite side of a sheet than the sensors so that the sensors may monitor an amount of light or an intensity of light shining through the sheet. For example, the amount of whiteness in greyscale may be an intensity of the light shining through the sheet. Some sensors may be free of lights. The one or more lights may be a bank of lights. The one or more lights may be located with each sensor and the lights and sensors may cooperate together. The lights may work with any of the sensors. The one or more lights may be a bank of lights. One or more lights or a plurality of lights may be aligned along or within the wet end, press section, dryer section, calender section, reel, or a combination thereof of the paper machine. The lights may produce day light, white light, bright white, led light, or a combination thereof. The one or more lights may assist the monitoring system so that the monitoring system may generate and send signals to the control system.

The control system may function to change or adjust one or more paper machine settings or to provide an alarm to a user. The control system may be connected to a monitoring system taught herein. The control system may vary the speed of the wire, angle of the foils, height of the foils, speed of stock coming out of the head box, stock jet angle, amount of suction being applied to one or more sections, vacuum levels, slice opening, stock jet speed, wire speed, jet to wire ratios, temperature of the stock, head box consistency, pressure of one or more press rolls, vacuum of a uhle box, temperature of a dryer, tightness of a felt (either press felt or dryer felt), pressure of calenders, speed of a reel, amount of fluid in a water box, or a combination thereof. The one control system may be an automatic control system, a manual control system, or both. The one or more control systems may adjust an activity line, a stock activity line, or both. The one or more control systems may move a movable sensor. The one or more control systems may communicate between two or more sensors; a sensor and a light; a level device and a sensor; an activity line and a sensor or a controller; or a combination thereof. The control system may include one or more processors, one or more microprocessors, or both that analyze a plurality of images taken by the sensors and correlate the sensors to one or more dry end tests so that wet end changes may be made to effect one or more dry end tests. The control system may monitor in real time.

The control system may be a closed loop control system. The control system may adjust the paper machine for changes in furnish, ambient temperature, freeness, stock temperature, grade, caliper, or a combination thereof. The control system may calculate positions of the components of the paper machine based upon measurements form the monitoring system, input measurements from operators, upstream monitoring equipment, or a combination thereof. The control system may calculate formation. The control system may convert formation to a number so that formation from location to location may be compared. The control system may provide real time feedback to a change. For example, if a speed of the paper machine is increased then formation changes can be monitored in real time to see how formation changes due to the speed change. The control system may adjust for ambient lighting conditions. For example, if it is night then the control system may measure the activity differently than if it is day outside. The lights may flood the monitoring region so that the time of day and ambient light do not affect the measurements. The control system may be part of a distributed control system (DCS). The control system may include formation monitoring, provide graphical formation representations, indicate formation changes, provide numerical formation representations, images, or a combination thereof. The control system may be part of the monitoring system. The control system may be in communication with one or more controllers.

The one or more controllers may be in communication with one or more components such as the head box, foils, groups of foils, wire, suction boxes, couch roll, breast roll, dilution controllers, angle adjustable foils, height adjustable foils, steam boxes, temperature control devices, press rolls, dryer rolls, uhle boxes, calender rolls, a reel, seed control, a location therebetween, or a combination thereof. The one or more controllers may be manually controlled, automatically controlled, or both. Each component (e.g., sensor, foil, foil motor, head box motor, slice opening, steam box, activity shower, nip, press roll, uhle box, calender roll, reel, dryer can, vacuum box, steam shower) may include a controller so that each component may be controlled independently or individually without reference to other components. The controllers may be remotely controlled (e.g., by a DCS, remote, or tablet). The controllers may be controlled by a wire. The controllers may be wirelessly controlled. The controllers may be locally controlled (e.g., a user standing by the paper machine manually actuating the controller or pressing a button). The controller may be controlled based upon stock activity, amplitude, size, scale, duration of activity, formation, a formation number, a formation change (e.g., delta) or a combination thereof. The controller may be a proportional controller, integral controller derivative controller, Proportional Integral Derivative (PID) controller, or a combination thereof. The controller may control from region to region.

The monitoring regions may be predetermined regions, standard regions, or both. The monitoring region may be a section in the cross-machine direction. One or more monitoring regions may be located in each section of a paper machine. Preferably, some or all of the sections may include some or a plurality of monitoring regions. The monitoring region may have a dimension in the cross-machine direction and a dimension in the machine direction so that an area is formed. A plurality of monitoring regions may exist in the cross-machine direction. The plurality of monitoring regions may exist in the machine-direction. A plurality of monitoring regions may be located side by side and span across the cross-machine direction. The monitoring regions may be aligned with an activity line so that spouts above a predetermined activity line can be measured in each monitoring region. The monitoring regions may be broken up into a plurality of sub-regions or pixels. The monitoring regions may span between the head box and the activity line. The monitoring regions may have a length that is equal to the length of a foil section, a press section, a dryer section, a calender section, a reel, or a location therebetween. The monitoring regions may have a width that is equal to ⅛ or more, ¼ or more, ½ or more of a cross section of a paper machine. The monitoring regions may have a width that is equal to a width of the paper machine or less or about ¾ or less of a cross-section of a paper machine. The monitoring region may cover any standard area. An area of about 0.25 $m^2$ or more, about 0.5 $m^2$ or more, about 1 $m^2$ or more, about 2 $m^2$ or more, about 10 $m^2$ or less, or about 5 $m^2$ or less may be monitored. The monitoring regions may be in the middle of the paper machine, on an edge of the paper machine, may be from one edge to a second opposing edge, or a combination thereof. The monitoring region may monitor a height above the monitoring region (and the area) of the sheet or wire. The height monitored may be about 1 cm or more, about 2 cm or more, about 5 cm or more, about 10 cm or more, about 100 cm or less, about 75 cm or less, or about 50 cm or less above an activity line, wire, sheet, or a combination thereof. The height monitored may extend above and below an activity line. For example, the if the sheet or wire is at 0 then a region above and below may be monitored (e.g., 5 cm above and 5 cm below (i.e., −5)). The height monitored above the activity line may be equal to a height monitored below an activity line. Each of the monitored regions may be displayed on a formation monitor.

The formation monitor functions to display real time formation, formation trends, formation images, graphical formation representations, numerical formation representations, or a combination thereof. Each section may include a screen, a window, a portion of a screen, or a combination thereof within the formation monitor. The formation monitor may be a graphical user interface that displays real time formation information so that current formation of formation trends may be monitored. The formation monitor may display graphical formation representations, formation changes, numerical formation representations, images, or a combination thereof.

The graphical formation representations function to demonstrate and track formation over a predetermined period time. The graphical formation representations may track changes in formation over a period of 5 minutes or more, 10 minutes or more, 30 minutes or more, 1 hour or more, 12 hour or more, a day or more, or even indefinitely. The graphical formation representations may be varied depending upon a preference from user to user but at a minimum may track from shift to shift. The graphical formation representations may be a plot of formation over time. The graphical formation representation may graphically illustrate if there is a formation change. The graphical formation representation may indicate if there is a step change or a gradual change over time. For example, if a formation change is noticed then a user or the monitoring system may determine if some machine change was made which caused the formation change due to the steepness of the curve. In another example, if the machine is slowed down formation may get worse and this formation change (e.g., delta) may be graphically illustrated as a steep change in formation. In another example, if a formation change is more gradual but the formation change can be seen due to the delta increasing gradually over a window (e.g., 30 minutes) then some other processes may have caused this change and may be explored (e.g., a change in chemicals, a change in furnish, a change in stock temperature). The graphical formation representation may be formed in real time based upon formation numbers which may be displayed as numerical formation representation. The formation numbers may be an average, a difference in a range, a median number, a number that is calculated and then multiplied by a multiplier, or a combination thereof. The formation numbers may be an integer from 1-100. The formation numbers may be any number from 1-100 that is rounded to the nearest hundredth decimal place. The numerical formation representation may be a real time number is displayed as each image is analyzed and categorized in real time. Thus, for example, if an operator looks and sees the numerical formation representation is a 20 the operator may understand that the machine is running well. However, if the operator sees periodic spikes where the numerical formation representation jumps to 50 and then falls rapidly the operator may seek to see what is causing these formation changes.

The numerical formation representation functions as a real time numerical representation of what a perceived formation is at that moment in time. The numerical formation representation may be calculated based upon measurement and categorization of the various grey scale measurements being taken. Each image may be analyzed, categorized, measured, or a combination thereof to provide a numerical formation representation for each image.

The monitoring system may monitor and/or control with a method. The method may include one or more steps performed in any order. The method may monitor the stock movement or stock activity. The stock activity, formation, or both may be compared to a reference stock activity, reference formation, or both. The stock activity, formation, or both may be compared to a saved stock activity, a saved formation, or both from a prior run of a paper grade. The stock activity, formation, or both may be compared to a saved stock activity, formation, or both when a wire is in a similar worn condition. For example, if the wire is 30 days old then the stock activity is compared to a reference activity on the paper machine when the wire is 30 days old. A change between the monitored activity and the reference activity are compared. The change is compared to a predicted formula, a predicted change, or both. The change from run to run may be used to adjust the settings to a default setting or a prior setting. The change may be a "delta" during the current run. For example, if formation is measured in a first location to have a value, at a second location to have a similar value, and at a third location where the value drastically changes then this delta provides feedback as to where the deviation occurred.

The value may be provided as a numerical value. The value may have a range from 1 to 100. A score of 1 may mean good formation and a value of 100 may mean poor formation. Thus, the formation score from point to point to point may all be monitored to understand if a change (i.e., delta) occurs. For example, if the value is 10, 10, and then 20, the operator and control system will know that some variation changed that caused formation to be reduced by 10 points. The method may include multiplying the numbers by a multiplier depending on the grade so that the numerical values may be compared from grade to grade. The multiplier may be calculated based upon an empirical opacity range or a theoretical opacity range. For example, a thicker sheet may have a smaller opacity range than a thinner sheet and may require a lager multiplier (e.g., correction) to correlate the numerical value from grade to grade. A change can then be made between the second location and the third location to change formation or to undue a chance that caused the delta. The numerical score may correlate to stock activity or may correlate stock activity to formation. Thus, stock activity may be correlated to a numerical value so that a stock activity numerical value may be compared to a formation numerical value.

The method may include a step of categorizing the stock activity, formation characteristic, or both. The stock activity may be categorized into primary activity, secondary activity, tertiary activity, or a combination thereof. The stock activity may be used to predict the position of the components on the paper machine to lower the variation or make changes on the paper machine, improve formation, or both. The change is compared to one or more stock movements and the stock movements after the change are predicted. If the change is reduced to zero the monitoring system may predict the impact on final properties of the paper, the formation of the paper, or both. The monitoring system may predict paper properties based upon the positions of the components on the paper machine, or the movement of the components on the paper machine (e.g., foils, head box, suction, speed, or any others discussed herein). The method may include a step of predicting paper properties. The method may include a step of comparing the predicted paper properties to a target sheet formation, calculating a formation error, calculating a numerical formation representation, a numerical value, calibrating the numerical value from grade to grade, categorizing each pixel or sub-region within a greyscale, or a combination thereof. The method may include a step of correlating stock activity to formation. The method may numerically quantify stock activity so that a delta may be determined relative to formation. For example, if the stock activity is quantified to a 15 and the formation before the dryers is a 30 then it may indicate that something has affected formation. The method may compare the formation value from location to location to discover a delta. The method may include a step of taking action when a delta is over a predetermined amount. A user may compare a numerical formation representation to an image to verify that the system is working properly. A graphical formation representation may be displayed so that formation changes may be viewed over time.

The method may include a step of comparing predicted paper properties to paper properties measured at the dry end. The monitoring system may predict paper properties based upon activity, a ratio of primary activity to secondary activity and/or tertiary activity, formation, or a combination thereof. The monitoring system may use all of the activity measurements to derive a numerical value. The monitoring system may indicate where adjustment is needed so that a user may make an adjustment. The monitoring system may indicate two locations that bookend where the adjustment is needed. For example, the monitoring system may indicate that a good measurement was taken at a first location and a high delta measurement was taken at a second location and thus something therebetween is adversely affecting formation. The user may make adjustments from a distal location from the paper machine, from proximate to the paper machine, or both. The monitoring system, control system, or both may automatically make adjustments. The method includes a step of a user inputting a desired adjustment to one or more paper machine components (e.g., foils, head box, etc.) from a remote location, a proximate location, or both. The monitoring system may begin review at the head box and continually monitor as the sheet moves towards the dry end as the activity changes and impacts are monitored by monitoring formation. A new target formation or properties are calculated based upon the calculated changes. A new predicted formation is calculated based upon the change in the paper machine components. If a target formation is not achieved then the steps may be repeated one or more times until target formation is achieved. The difference between the predicted and the actual stock movement, paper machine properties, or both are calculated. The difference between the predicted and the actual may be used to correlate to a formation error or a change in formation (delta). The difference between the predicted value and the actual value may be used to move one or more components of the paper machine. The difference between the predicted value and the actual value may be used to calculate a distance of movement of the foils, the position of the foils, the speed of the wire, the speed of the stock, the slice opening size, the amount of vacuum, temperature of dryer cans, pressure of a press, uhle box, amount of water removed, calender pressure, reel speed, water box, steam showers, or a combination thereof. The process may be repeated for each section of the paper machine. The process may begin at the head box, the slice opening, the first foil section, or a combination thereof. The process may monitor a paper machine with the monitoring system taught herein, and control the paper machine with the control system taught herein. The control system, controller, monitoring system, or a combination thereof may include memory. The control system, controller, monitoring system, or a combination thereof may record positions of each component of the paper machine (e.g., foil positions, machine speed, slice opening, stock jet velocity). The method includes a step of changing one or more of the components to a pre-recorded position in anticipation of a grade change, during a grade change, or at a beginning of a grade change. The numerical formation representation may predict paper properties. The numerical formation representation may demonstrate that one section of a paper machine is responsible for causing a delta in formation. The numerical formation may be an average of a combination of x measurements or calculated by a rolling average over the last x measurements (where x may be 5 or more, 10 or more, 25 or more, or 50 or more, or 100 or less). The monitoring system may make changes based upon a delta or formation changes. The monitoring system may set alarms when a delta exceeds a threshold (e.g., 5 percent, 10 percent change in the past 5 minutes or less or 3 minutes or less).

FIG. 1 is a side view of a paper machine 2. The paper machine 2 includes a control system 40 connected to a formation detection system 30 and a monitoring system 20. The paper machine 2 includes a wet end 18, a press section 100, a dryer section 120, a calender section 130, and a reel section 140. The wet end 18 includes a head box 4 that supplies stock 60 onto a wire 6 that is traveling in the machine direction 14 from a breast roll 5 to a couch roll 10. A light 22 and camera 24 monitor a cut-through 72 between the wire 6 and the headbox 4. The press section 100 include lights 22 and cameras 24 that monitor between press rolls. From the press section 100 the sheet 80 extends to a dryer section 120 including a plurality of dryer cans 122. The lights 22 and cameras 24 monitor the sheet within the dryer section 120. From the dryer section 120 the sheet extends into a calender section 130 (or finishing section). Lights 22 and cameras 24 monitor the sheet 80 before, during, or after nips between calender rolls 132. The sheet 80 extends from the calender section 130 to a reel section 140 where a final review of the sheet occurs by a light 22 and camera 24 before being wound around a reel 142. Some or all of the cameras 24 may be part of the monitoring system 20 and formation detection system 30. The monitoring system 20 and the formation detection system 30 are connected to a control system 40 and a controller 42 that control the paper machine 2.

Figure 2:
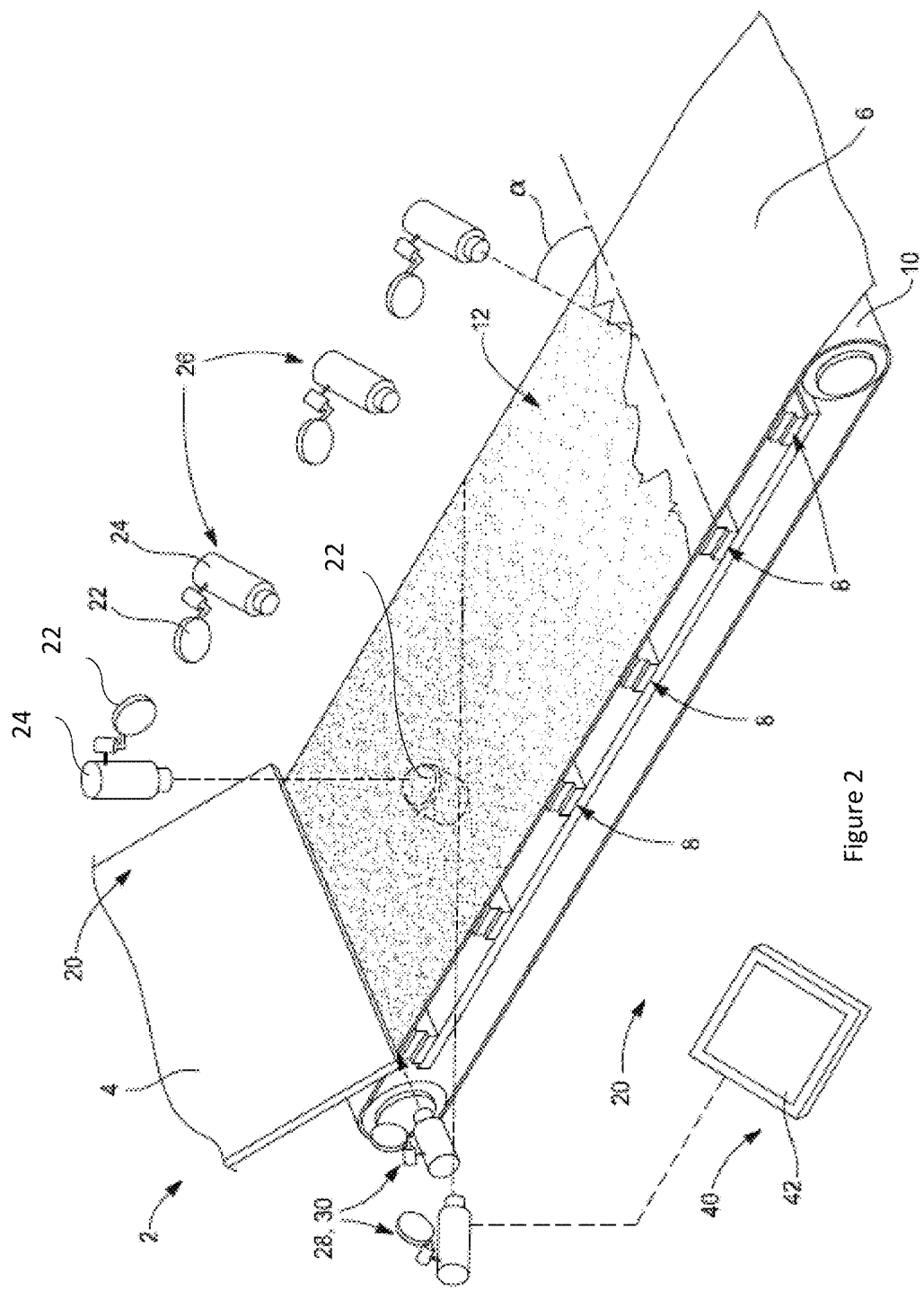
FIG. 2 is a perspective view of a wet end of a paper machine.

FIG. 2 illustrates a perspective view of a paper machine 2 that includes a monitoring system 20, formation detection system 30, and a control system 40. The paper machine 2 includes a head box 4 that puts stock (not shown) on a wire 6 as the wire 6 continuously moves. The wire 6 travels under the headbox 4 to receive the stock and then over a plurality of foil sections 8 that remove water from the stock which creates a dry line 12 in the stock. The wire 6 ends at the couch roll 10 where the wire 6 turns and extends in a reverse direction. The formation detection system 30, monitors one or more locations between the headbox 4 and the couch roll 10. As shown the formation detection system 30 includes a low angle sensor 28 that views the stock exiting the head box 4 and a location above and below the wire 6. The formation detection system 30 also includes a camera 24 and light 22 above the paper machine 2 with a light 22 below the sheet that monitors formation and correlates the formation with low angle sensor 28 along a side. The monitoring system 20 and formation detection system 30 as shown includes a plurality of lights 22, plurality of sensors 24 to monitor process conditions of the stock (not shown) along or across the wire 6. The monitoring system 20 and formation detection system 30 includes high angle sensors 26 and low angle sensors 28. The low angle sensors 26 are located substantially level with the wire 6. The high angle sensors 26 have a sight line that extends at an angle (a) relative to the wire or stock. The control system 40 including a controller 42 is connected to the monitoring system 20 and the paper machine 2 and preferably the foil sections 8 to control movement of the individual foils (not shown) within the foil sections 8.

Figure 3:
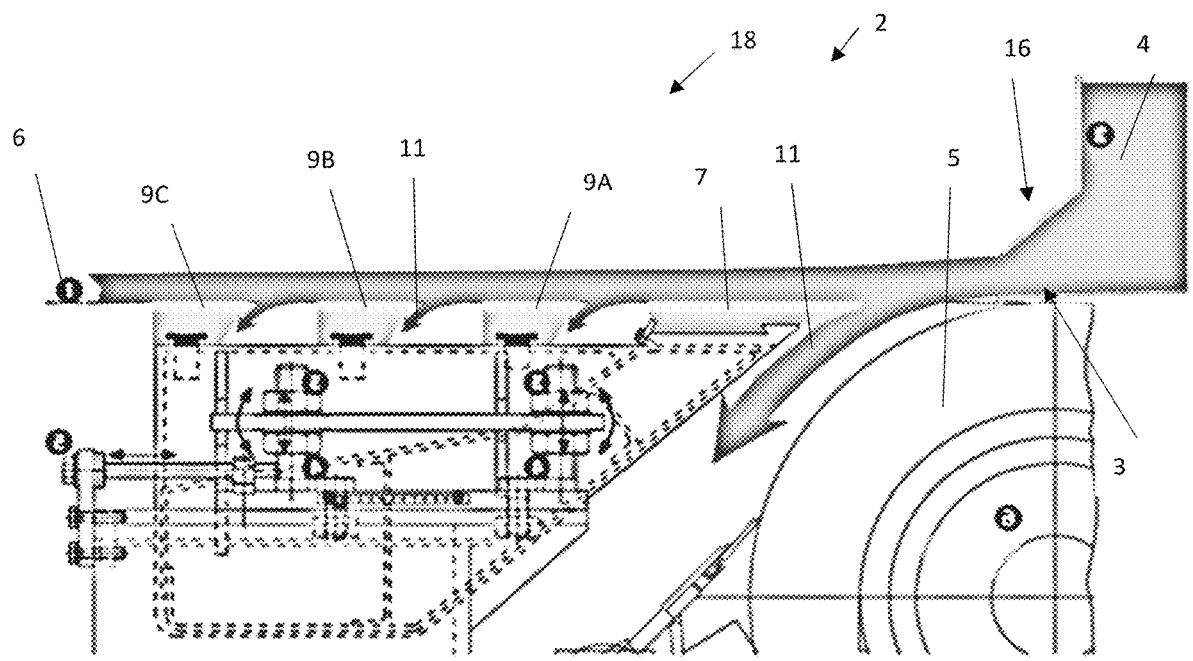
FIG. 3 is a side view of a cut through illustrating stock dewatering.

FIG. 3 illustrates a wet end 18 of a paper machine 2 including a head box 4 that moves stock through a slice opening 3 forming a stock jet 16. The stock jet 16 extends over the breast roll 5 and towards the wire 6 at an angle such that some water 11 is removed by passing through the wire 6 proximate to the forming board 7. The wire 6 then moves the stock across blades, which as shown are an angle adjustable foil 9A, a height adjustable foil 9B, and then a static foil 9C that remove water 11. The angle adjustable foils 9A and the height adjustable foils 9B each affect activity of the stock on the wire 6 based upon their respective position.

Figure 4:
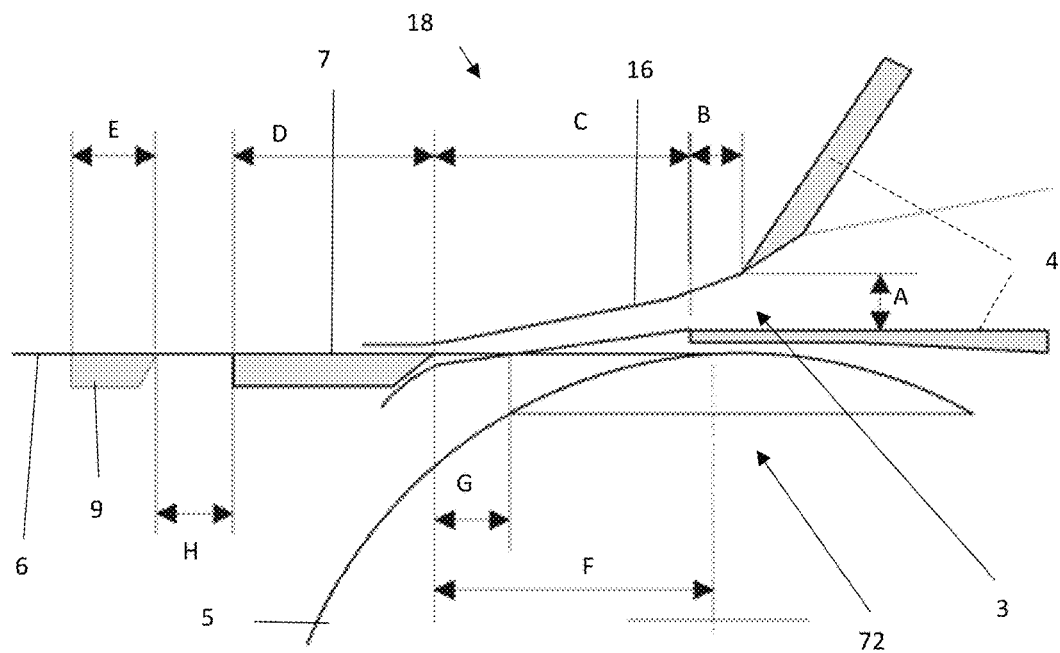

FIG. 4 illustrates the relationship of pieces of the wet end 18 relative to each other and how the formation detection system (not shown) controls formation and dewatering in the cut through 72. The head box 4 has a slice opening 3 with a gap (A) setting a height and a distance (B) a bottom portion of the head box 4 extends towards the forming board 7. The bottom portion of the head box 4 is located a distance (C) from the forming board 7, which has a length (D). An end of the forming board is located a distance (H) from a foil 9, which has a length (E). The forming board 7 is located a distance (F) from a center of the breast roll 5. The stock jet 16 extends at an angle so that the impingement of the stock jet 16 with the wire 6 is a distance (G) before the forming board 7. The distances depicted in FIG. 4 may be changed to change the formation. For example, the forming board 7 may be moved so that distances (G) and (F) are increased or decreased. The slice opening 3 may be varied so that distances (A) or (B) change and the stock jet 16 changes. The stock jet 16 may also be varied by an amount of pressure applied as the stock jet 16 exits the slice opening 3.

Figure 5:
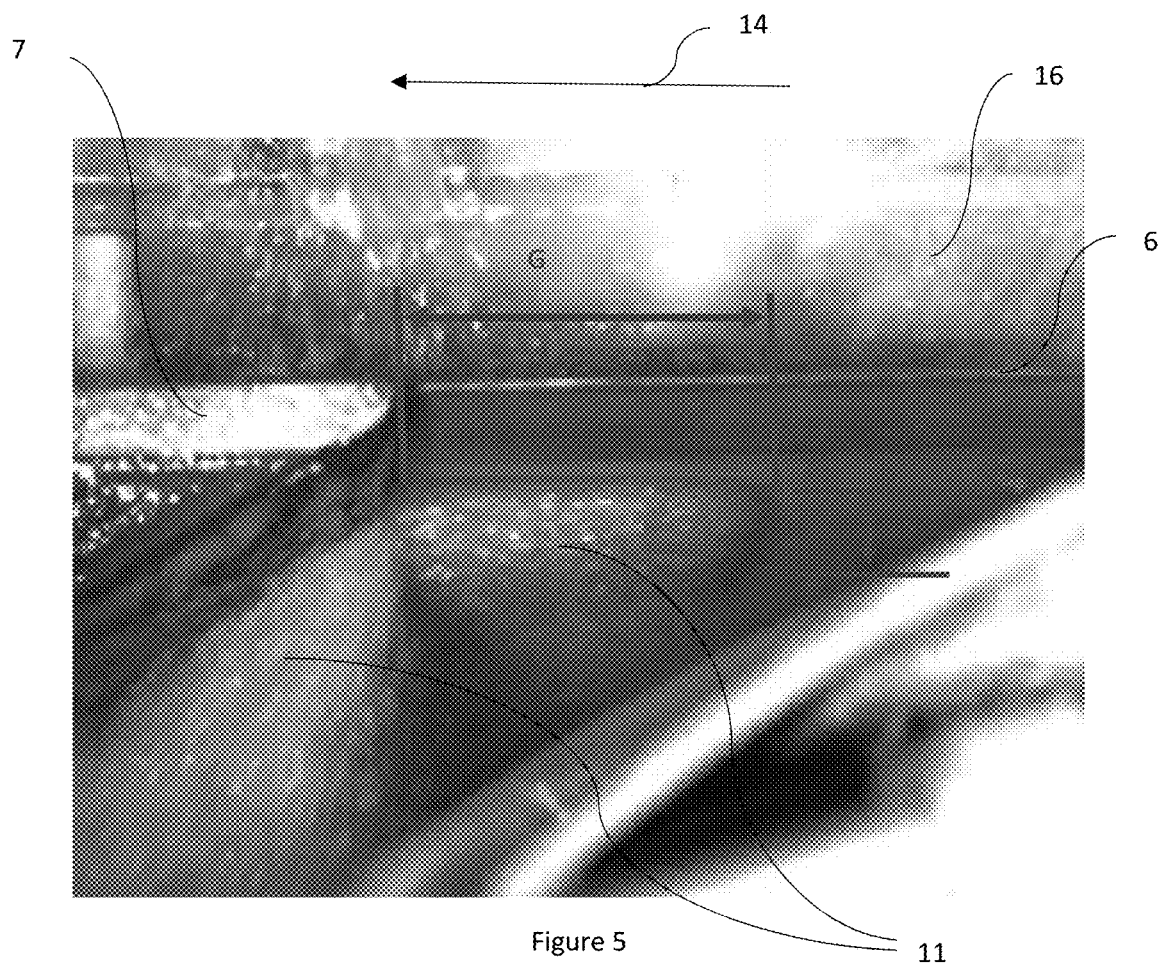
FIG. 5 is a picture of a cut through being monitored by the formation detection system.

FIG. 5 illustrates the stock jet 16 impinging the wire 6 as the wire 6 extends in the machine direction 14 towards the forming board 7. The impingement of the stock jet 16 with the wire 6 forms a first set of removed water 11, which extends through the wire 6 a distance (G) from the forming board 7. The distance (K) the removed water 11 passes through the wire 6 is also measured. The formation detection system (not shown) varies the distanced (G) and (K) to vary the formation of the sheet.

Figure 6:
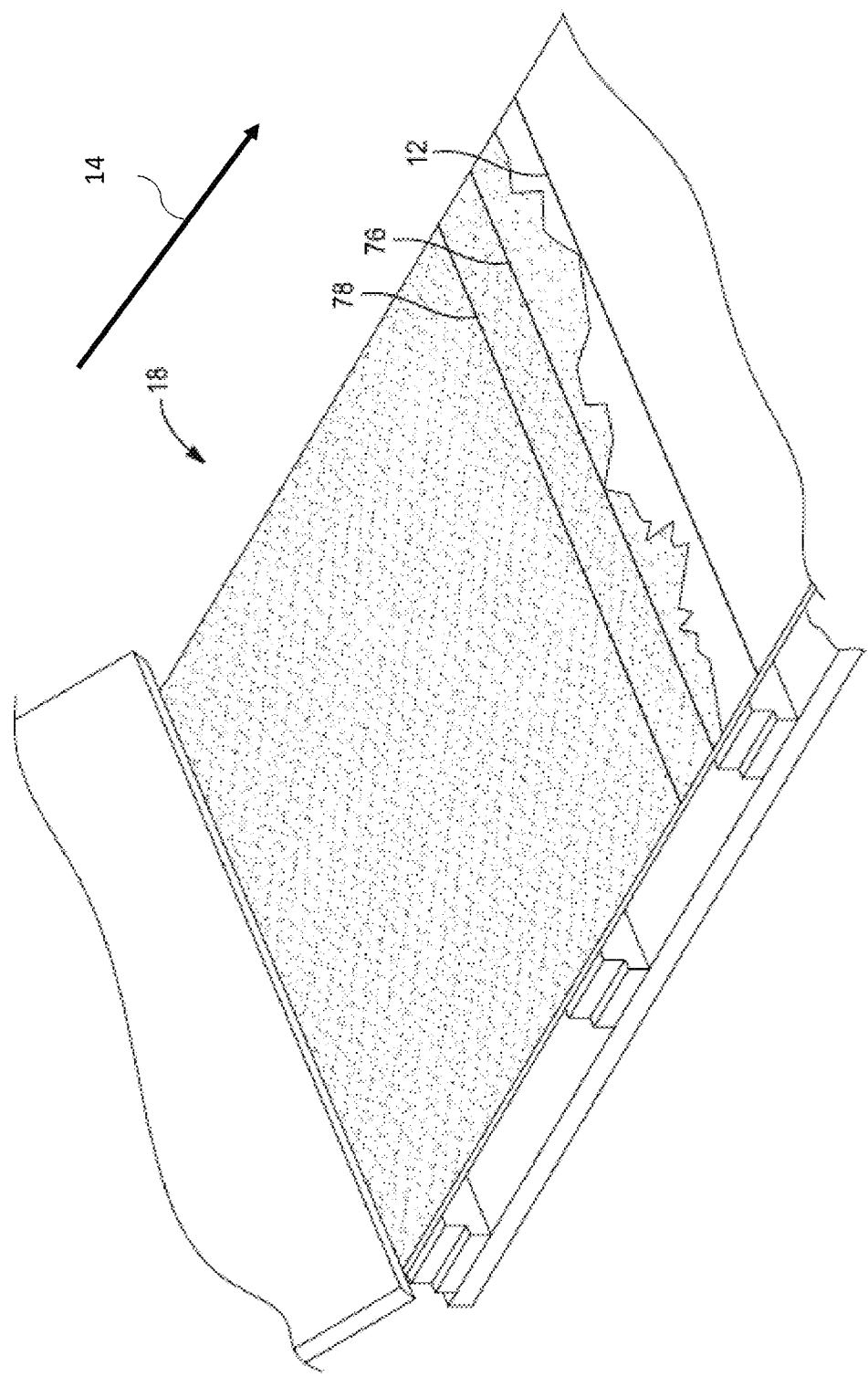
FIG. 6 is a perspective view of a dry line, wet line, and activity line.

FIG. 6 illustrates a dry line 12, wet line 76, and activity line 74 within the wet end 18 as the stock travels in the machine direction 14.

Figure 7A:
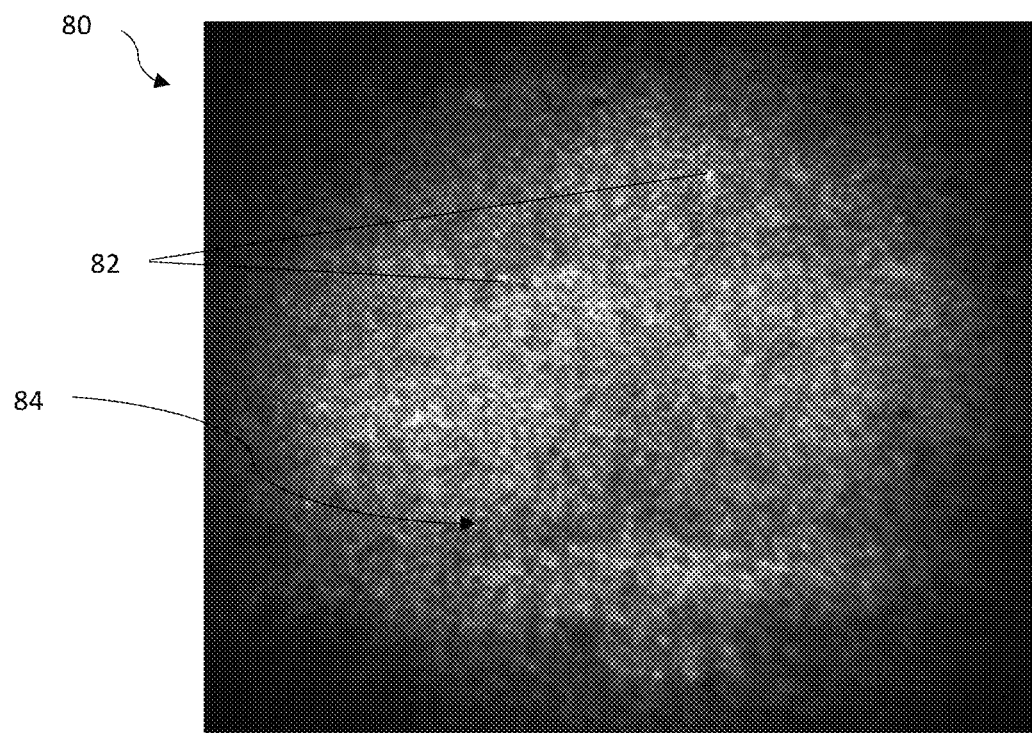
FIG. 7A is an image illustrating stock formation measured by the formation detection system.

FIG. 7A is an example of a formation of a sheet 80. The formation detection system (not shown) assists in detecting pin holes 82 and streaks 84 within the sheet 80 so that formation paper machine characteristics may be changed or adjusted to remove detected characteristics within a sheet.

Figure 7B:
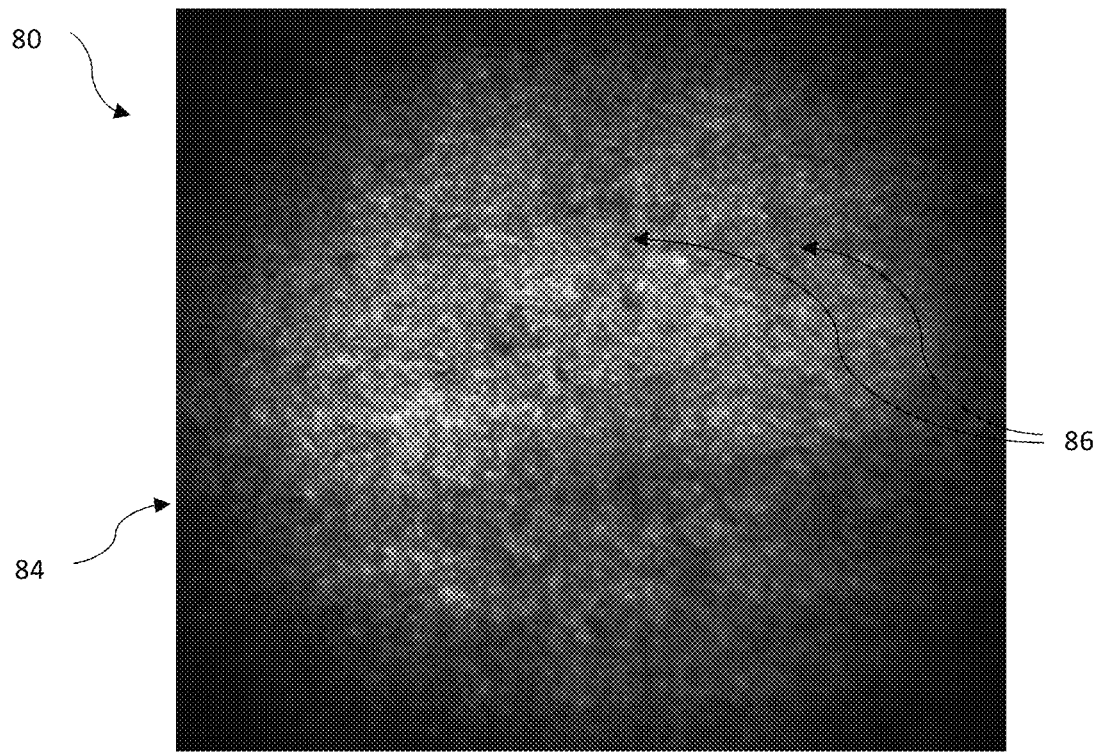
FIG. 7B is an image illustrating stock formation measured by the formation detection system.

FIG. 7B illustrates a sheet 80 where streaks 84 and headbox pulsations 86 are visible. The streak 84 is visible as a horizontal line (machine direction) of fibers. The headbox pulsations 86 are visible as a vertical line (cross-machine direction) of fibers.

Figure 8A:
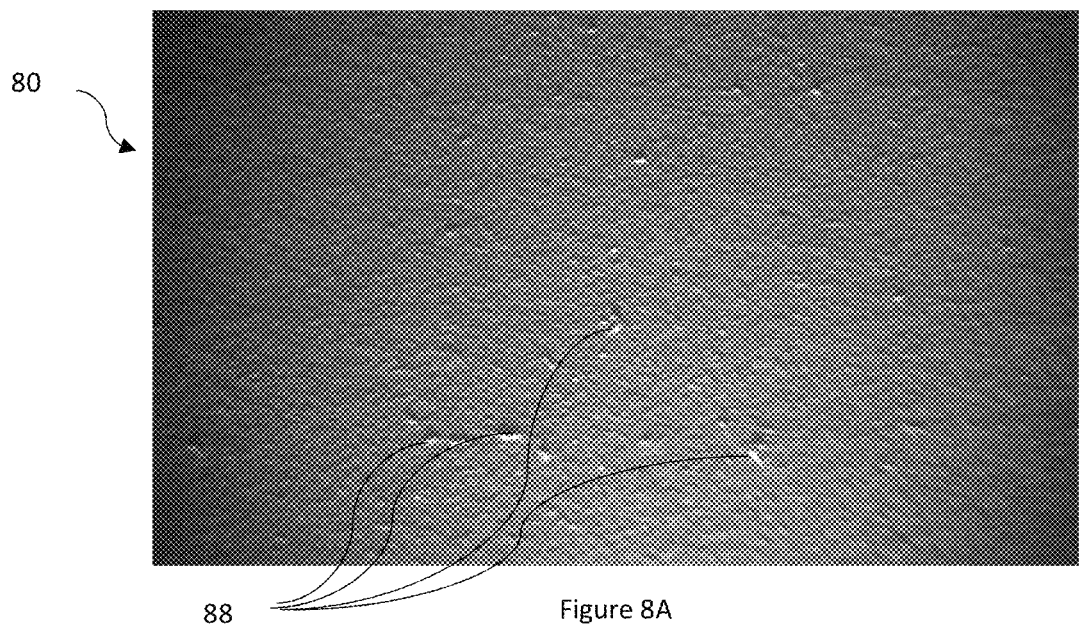
FIG. 8A is an image showing surface topography being monitored by the formation detection system.

FIG. 8A is a picture of a sheet 80 where topographical features such as flakes 88 are visible. The flakes 88 as shown are an indication that the sheet 80 is square.

Figure 8B:
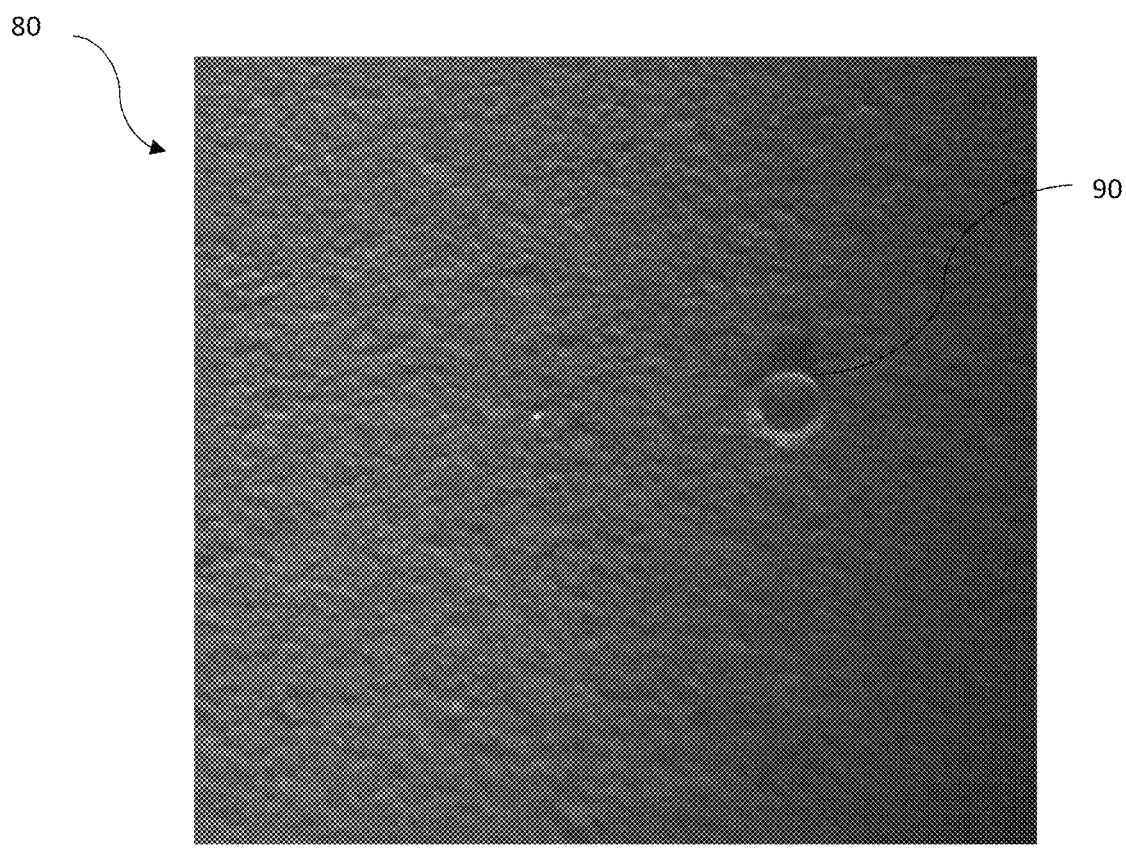
FIG. 8B is an image showing surface topography being monitored by the formation detection system.

FIG. 8B is a picture of a sheet 80 that includes topographical features such as a bubble or water drop 90.

Figure 9:
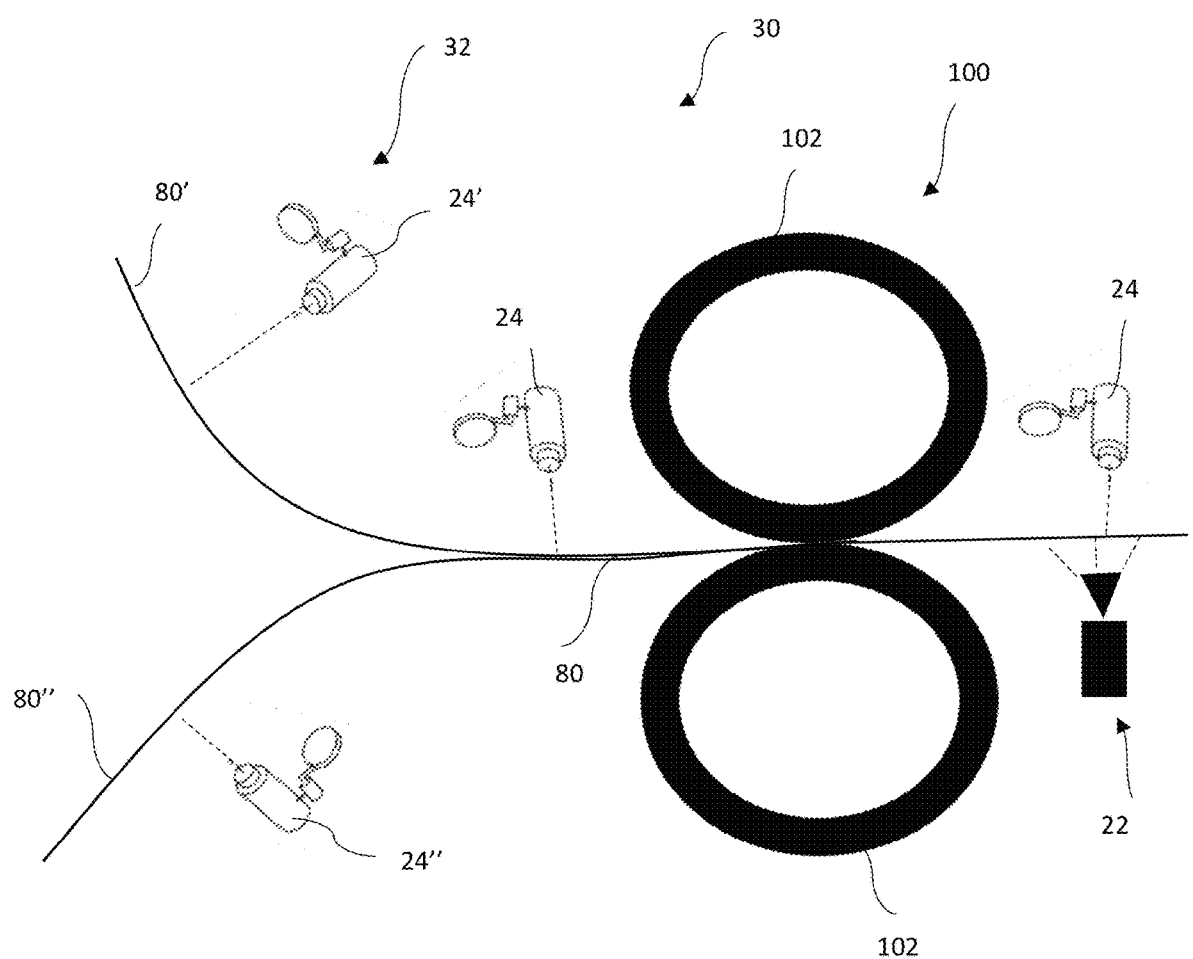
FIG. 9 illustrates the formation detection system monitoring formation of individual plies, monitoring combined plies, and them monitoring the combined plies after a press section.

FIG. 9 illustrates the formation detection system 30 including multi-ply sensors 32. The multi-ply sensors 32 have a first sheet 80' monitored by a first sensor 24' and a second sheet 80" monitored by a second sensor 24". The first sheet 80' and the second sheet 80" are combined together to form a sheet 80. The sheet 80 may be monitored by sensors 24 before a press section 100, after the sheet 80 passes through the press rolls 102, or both before the press rolls 102 and after the press rolls 102. A light 22 is located above and below the sheet 80 so that formation is visible. The light 22 may be above and below at any location or only be located on one side of the sheet 80.

Figure 10:
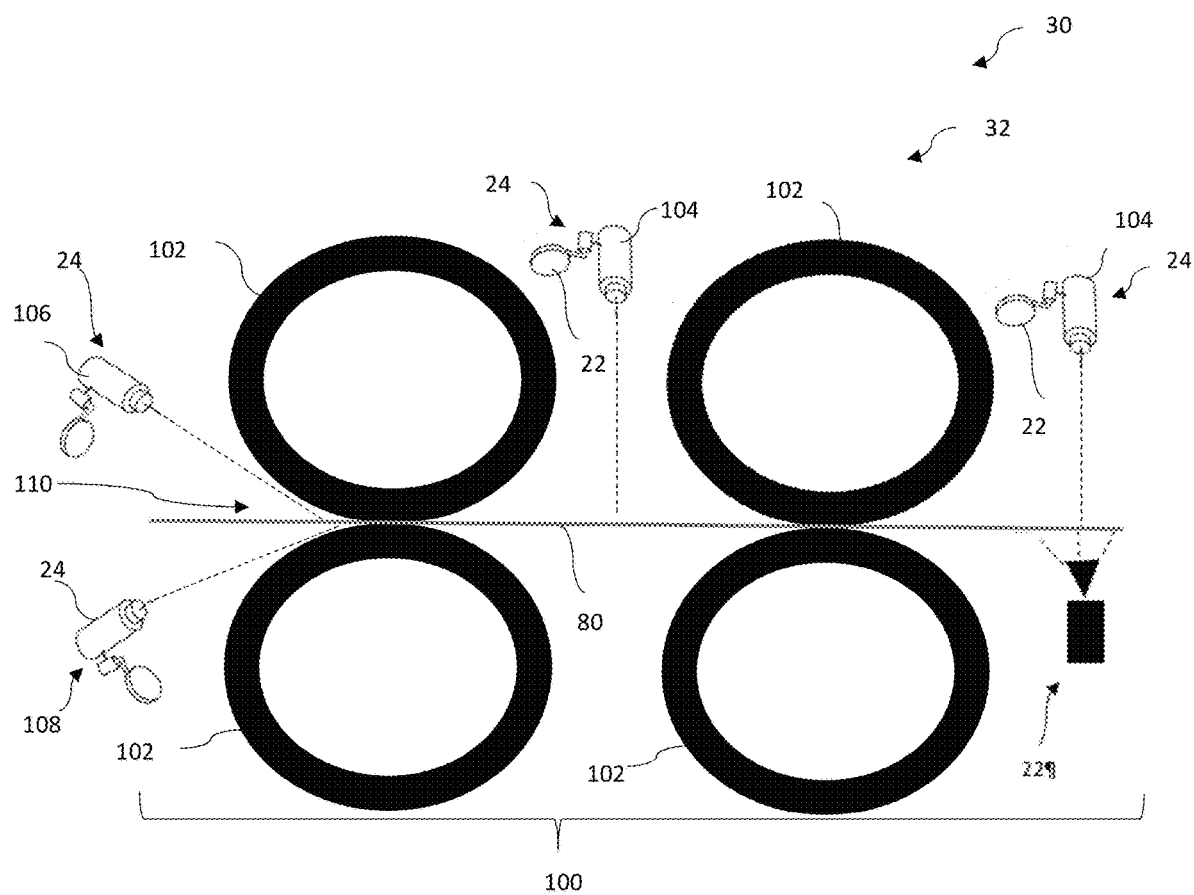
FIG. 10 illustrates monitoring of a sheet passing through a nip from a location above and below and monitoring the sheet after each nip of a press section.

FIG. 10 illustrates a press section 100 including the formation detection system 30. The formation detection system 30 includes press section sensors 34 which include one or more of overhead sensors 104 (which may be before, after, or between press rolls 102); high angle sensors 106 aiming towards a top of the sheet 80 entering a nip 110; a low angle sensor 108 aiming towards a bottom of the sheet 80 entering a nip 110; or a combination of the sensors 24 and lights 22. The light 22 may be above and below at any location or only be located on one side of the sheet 80.

Figure 11:
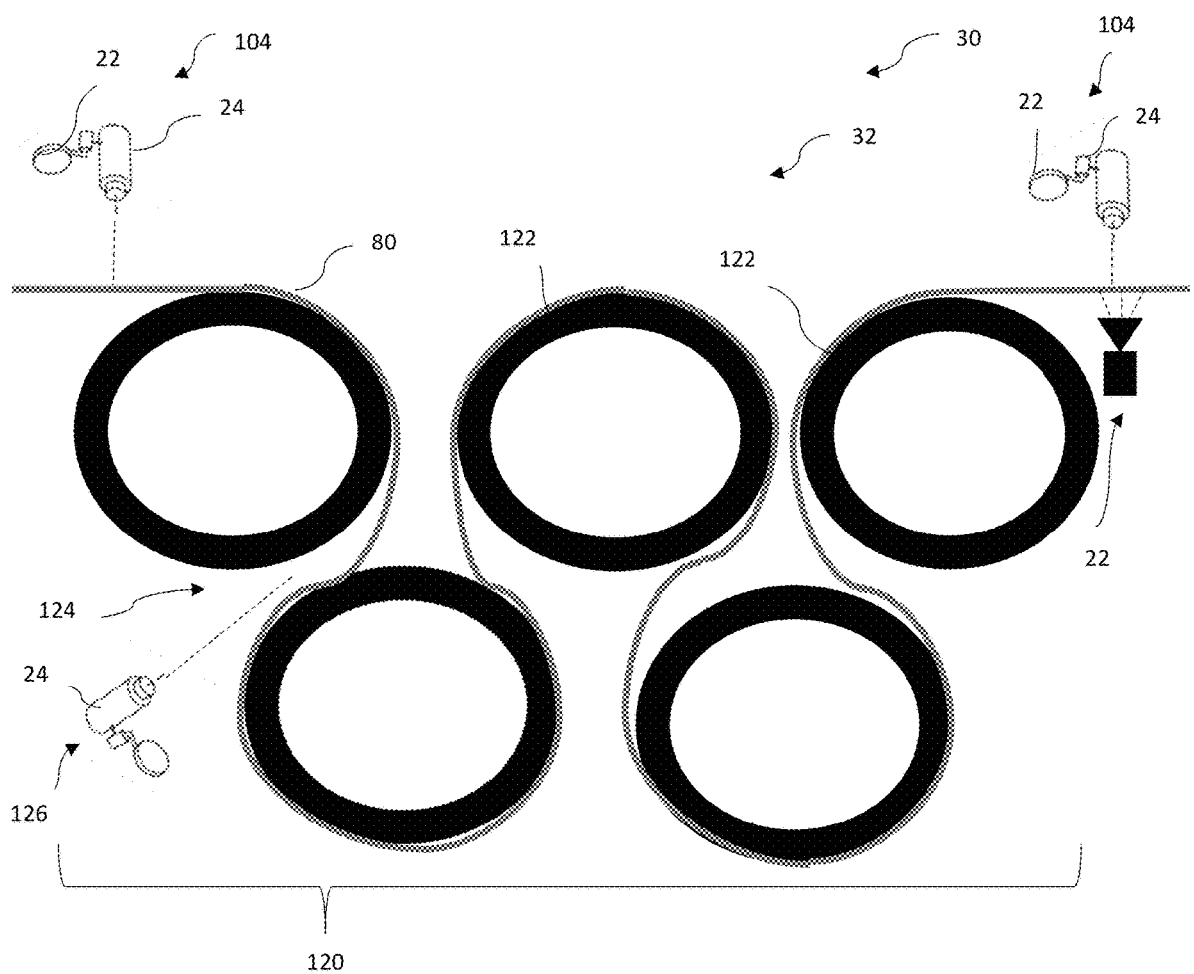
FIG. 11 illustrates the formation detection system monitoring as sheet passing through the press section.

FIG. 11 illustrates a dryer section 120 including the formation detection system 30, which may be multi-ply sensors 32. The formation detection system 30 includes sensors 24 including overhead sensors 104 and transfer sensors 126. The sensors 24 include lights 22 to illuminate the sheet 80 so that the formation is visible as the sheet 80 enters the dryer section 120, transfers between the dryer cans 122 (e.g., a transfer location 124 between dryer cans 122), after the dryer section 120, or a combination thereof. The light 22 may be above and below at any location or only be located on one side of the sheet 80.

Figure 12:
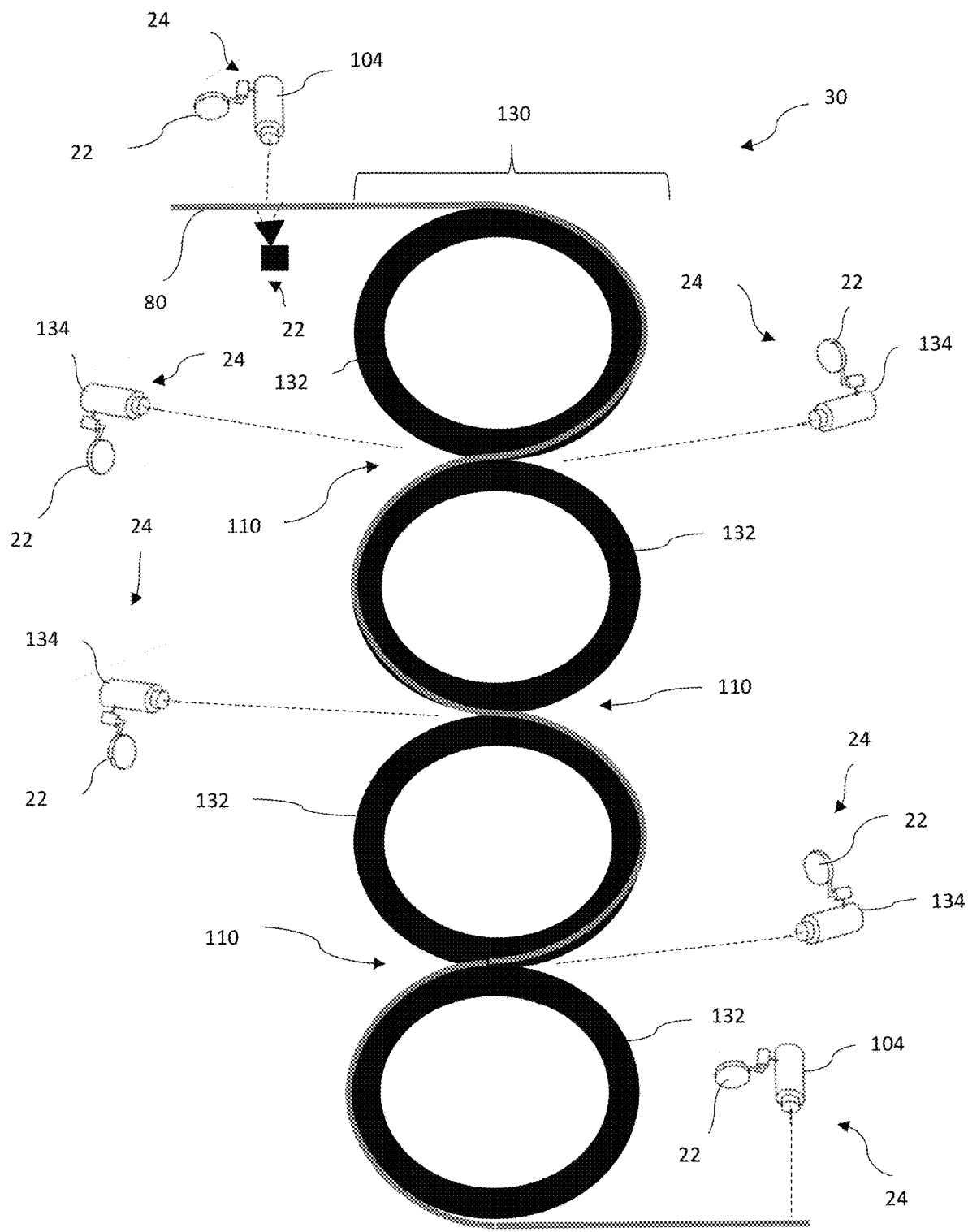
FIG. 12 is a side view of the formation detection system mounting the sheet as the sheet passes through a calender.

FIG. 12 illustrates a calender section 130 including the formation detection system 30. The formation detection system 30 includes overhead sensors 104 that look substantially normal to the sheet 80. The overhead sensors 104 include a sensor 24 and a light 22. As shown, a light 22 is also illustrated as being located below the sheet 80 in one location and is free of a section light. The calender rolls 132 include a nip 110 between the calender rolls 132. A nip sensor 134 is shown located before and after a nip 110. Some calender rolls 132 may only be on the lead in side of a nip 110. The sheet 80 extends through the nips 110 that may change some properties of the sheet 80 and the formation detection system 30 monitors changes to the sheet 80.

Figure 13:
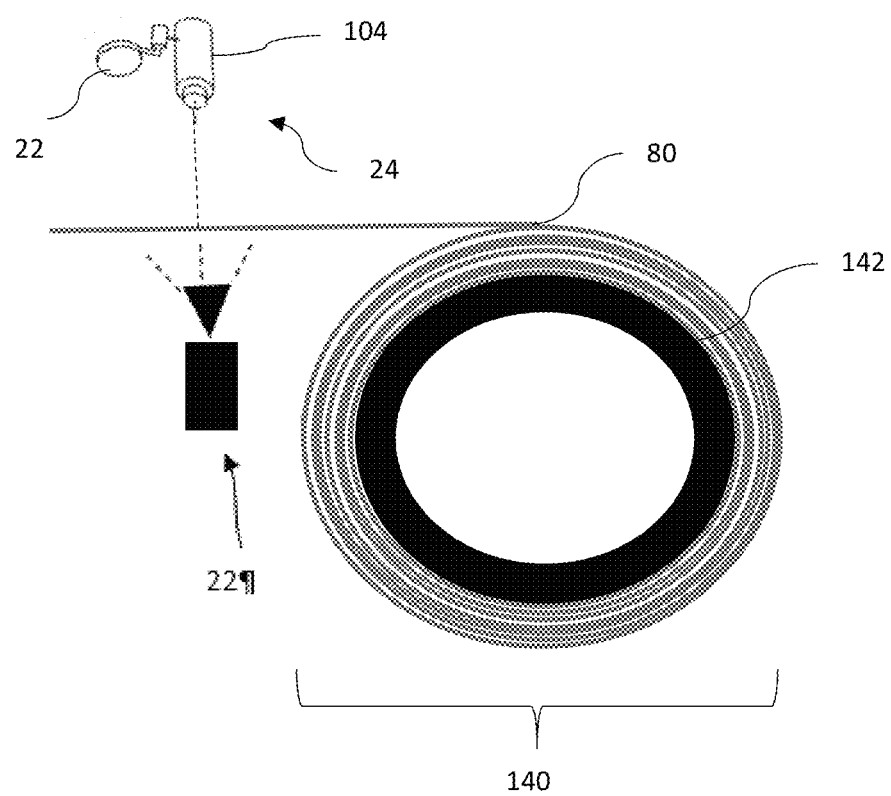
FIG. 13 is a side view of the formation detection system monitoring the sheet as the sheet is wound on the reel.

FIG. 13 illustrates a sheet 80 extending into a reel section 140 to wrap around a reel 142. The sheet 80 is monitored by an overhead sensor 104 that includes a light 22 and a sensor 24. As shown, a light 22 is also located below the sheet 80.

Figure 14A:
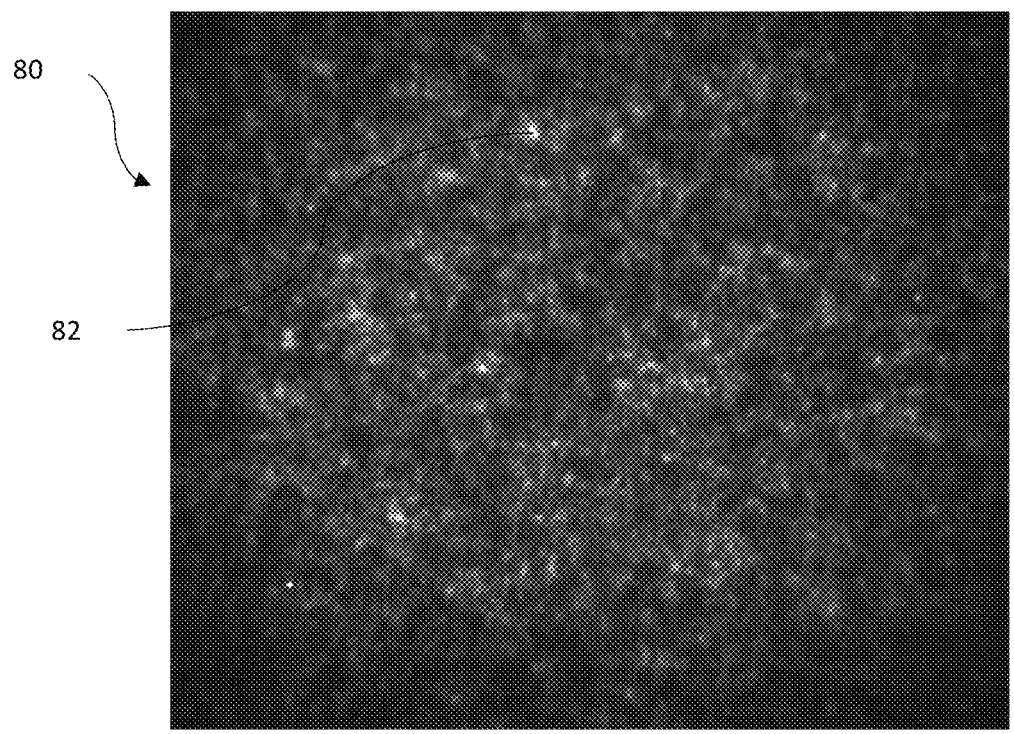
FIG. 14A is a picture of the formation of the sheet in the dry end.

FIG. 14A illustrates a picture of a sheet 80 with pin holes 82 visible.

Figure 14B:
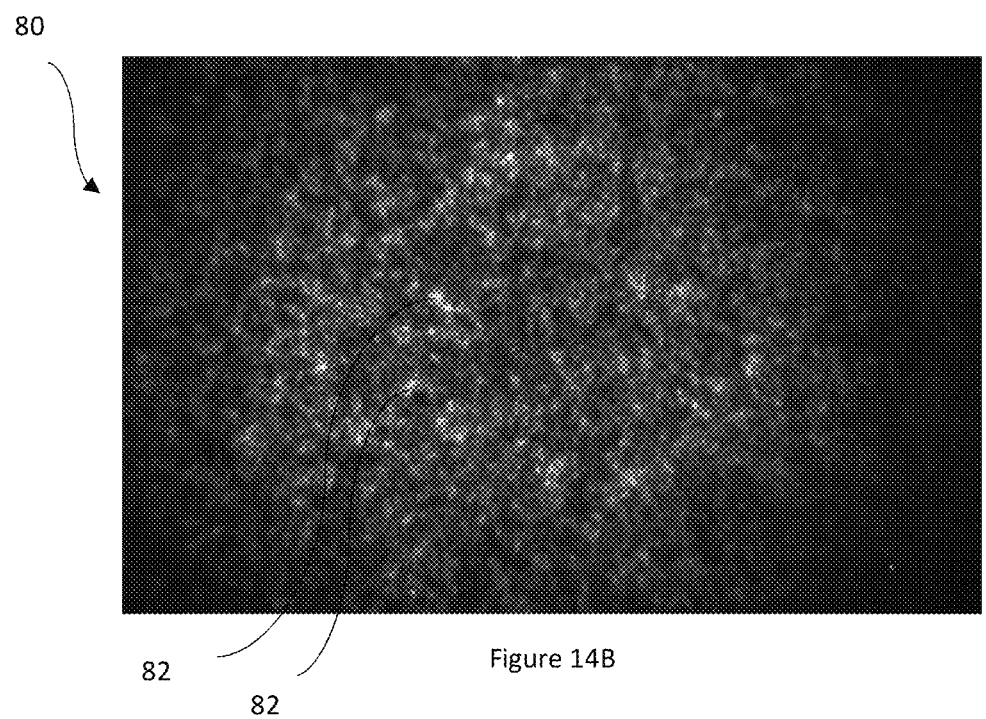
FIG. 14B is a picture of the formation of the sheet in the dry end.

FIG. 14B illustrates a picture of a sheet 80 with pin holes 82 show in the sheet 80 formation.

Figure 15A:
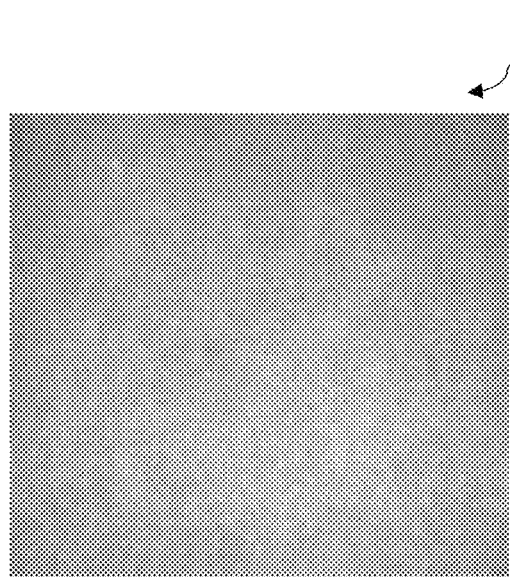
FIG. 15A is a picture of formation with a low score (e.g., good formation)
Figure 15B:
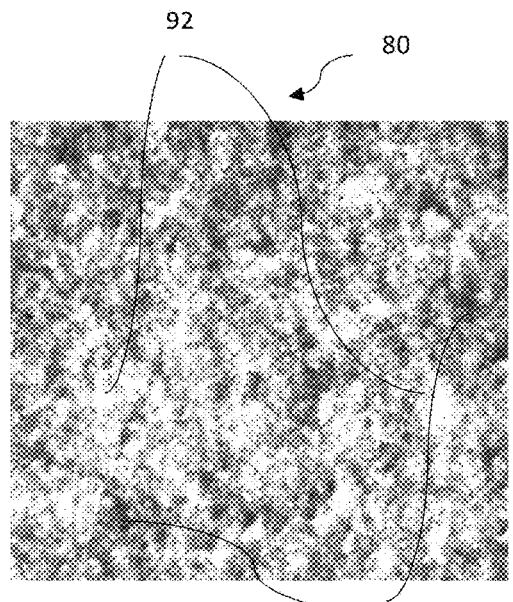
FIG. 15B is a picture of formation with a high score (e.g., poor formation)

FIG. 15A and FIG. 15B are side by side photos illustrating a sheet of paper 80 and differing formation characteristics. FIG. 15A is substantially uniform in opacity and is free of large light spots or large dark spots or regions. The sheet 80 looks substantially monochrome from edge to edge. FIG. 15B is a sheet 80 with a mottled appearance having large areas of light spots 92 and dark spots 94 so that the opacity varies depending on the relationship to the light spots 92 or the dark spots 94.

Figure 16A:
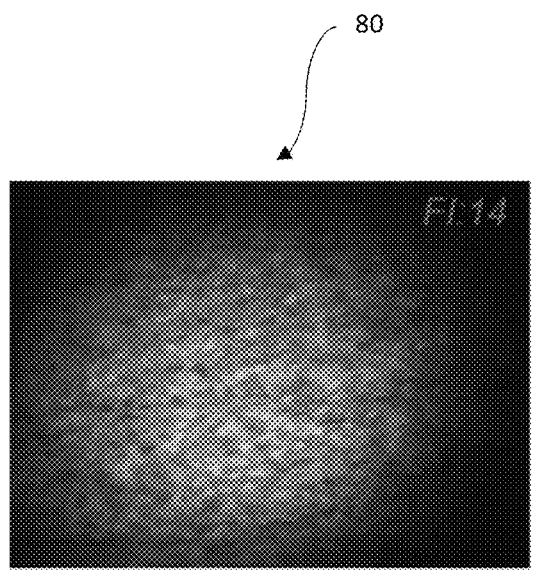
FIG. 16A is a picture of formation with a low score.
Figure 16B:
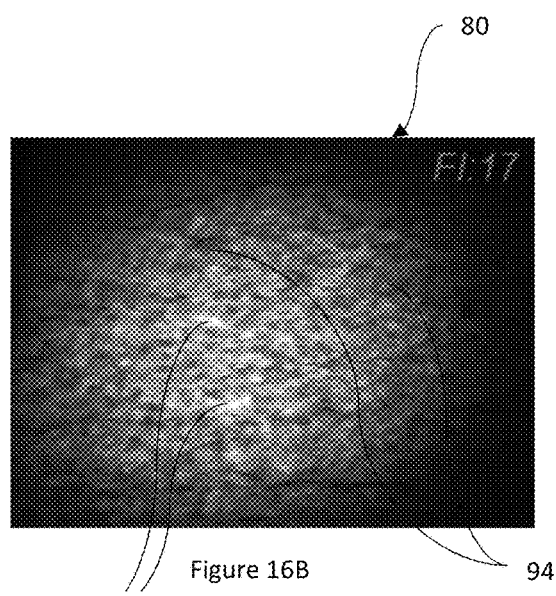
FIG. 16B is a picture of formation with a high score.

FIGS. 16A and 16B are another example of side by side photos depicting difference in formation of two sheets of paper 80. FIG. 16A is more uniform than FIG. 16B and does not include any large light spots or large dark spots. FIG. 16B is mottled and has large light spots 92 and large dark spots 94 representing poor formation in those areas.

Figure 17:
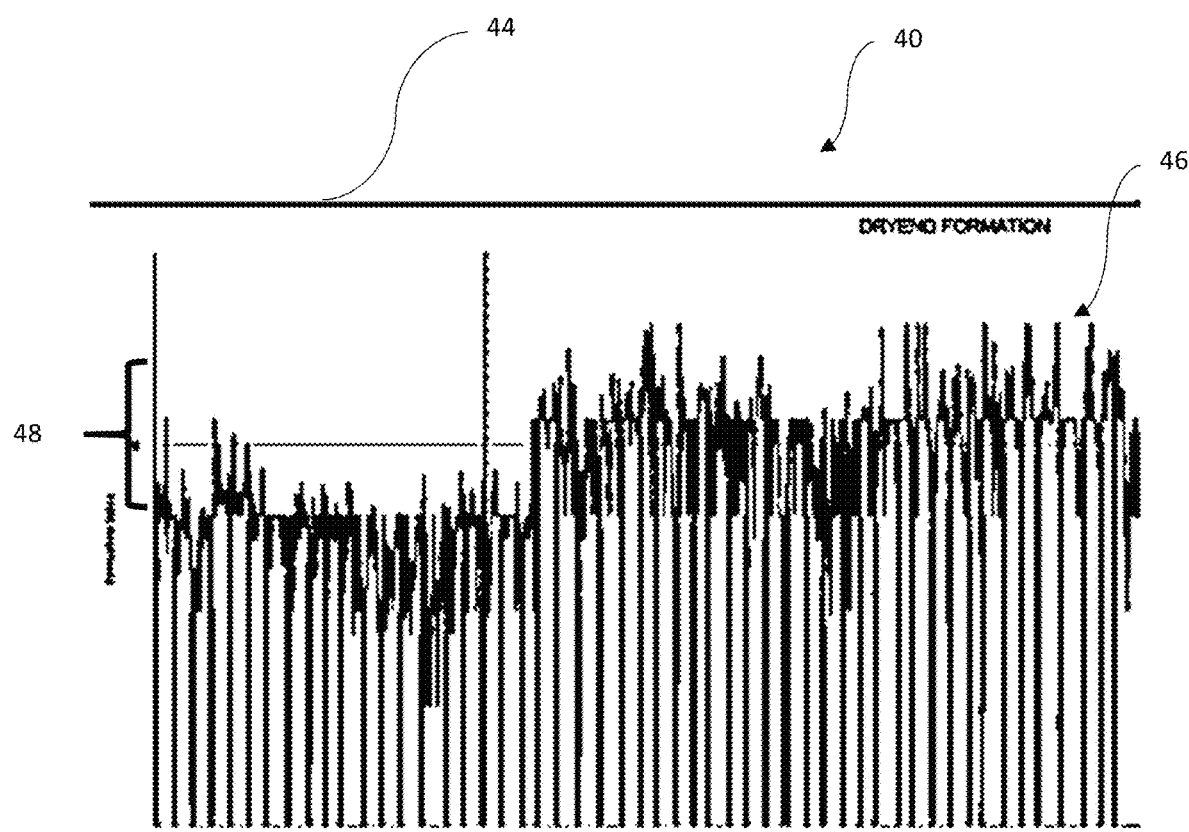
FIG. 17 is a graph demonstrating a change in formation of a sheet formed on a paper machine.

FIG. 17 illustrates a control system 40 having a formation monitor 44 tracking formation in real time and outputting a graphical formation representation 46 of the real time formation. As shown, the graphical formation representation 46 depicts a formation change at the monitored location, which as shown is at the dry end.

Figure 18:
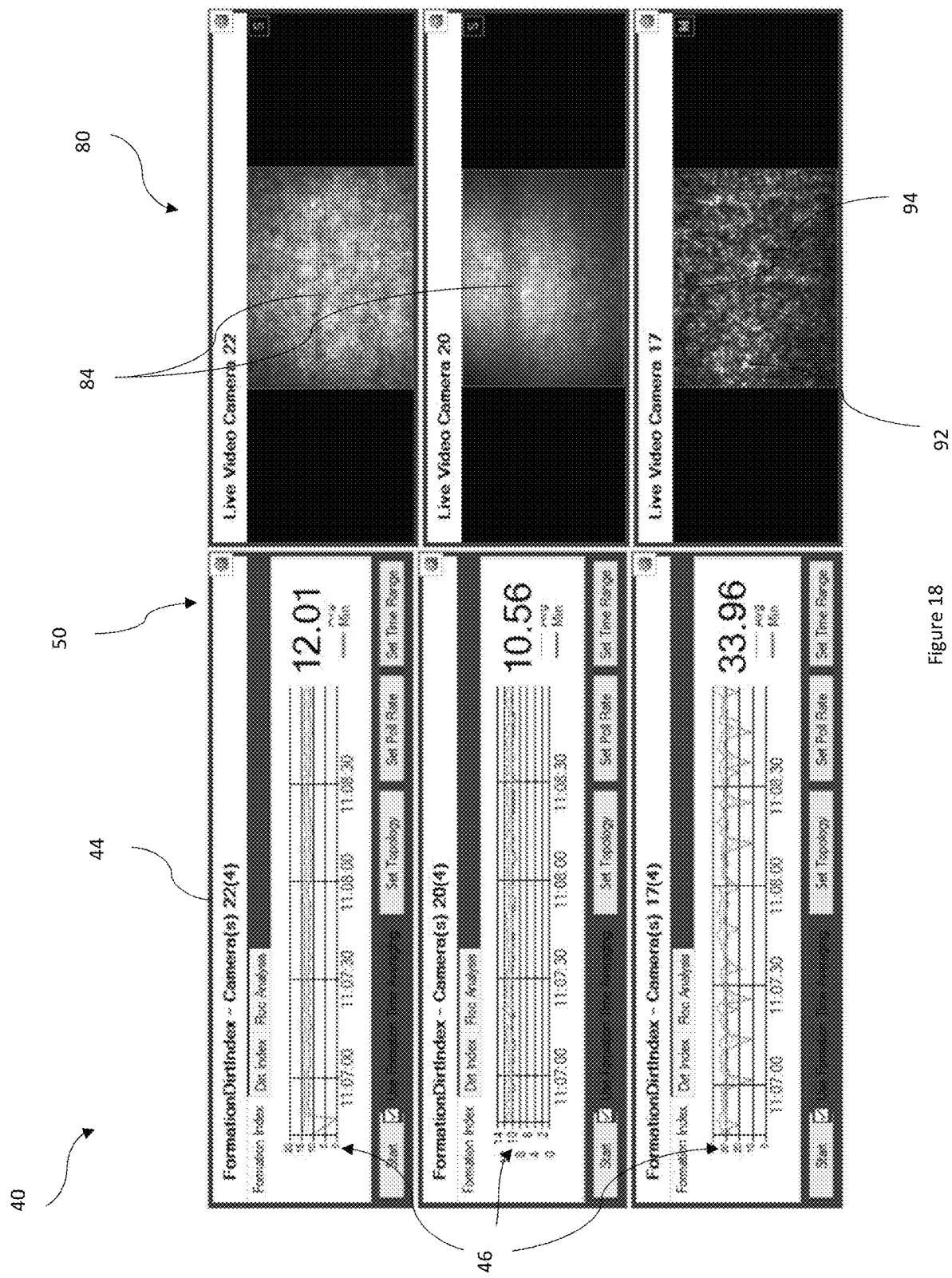
FIG. 18 is a screen graphical representation of a real time formation index measuring and scoring the formation at locations along the paper machine.

FIG. 18 illustrates a control system 40 including a formation monitor 44 displaying real time sheet 80 images, graphical formation representations 46, and numerical formation representations 50. The graphical formation representations 46 illustrate changes in formation over time so that an operator is able to see if the formation is trending in a direction or is stable. The numerical formation representation 50 provides a real time number that may be compared to an image to so that an operator may verify the number with the image (e.g., the operator may be able to see that calibration is off or the system is not working properly). Multiple locations may be compared simultaneously such that a step change in a numerical formation representation 50 may illustrate that formation is being changed by a certain section. As illustrated, the third section has changed by a factor of 3 relative to the first two section indicating that formation is being impacted between measurement 2 and measurement 3. The first two sheet 80 images depict a small streak 84 whereas the third sheet 90 image is mottled and has light spots 92 and dark spots 94.

Figure 19:
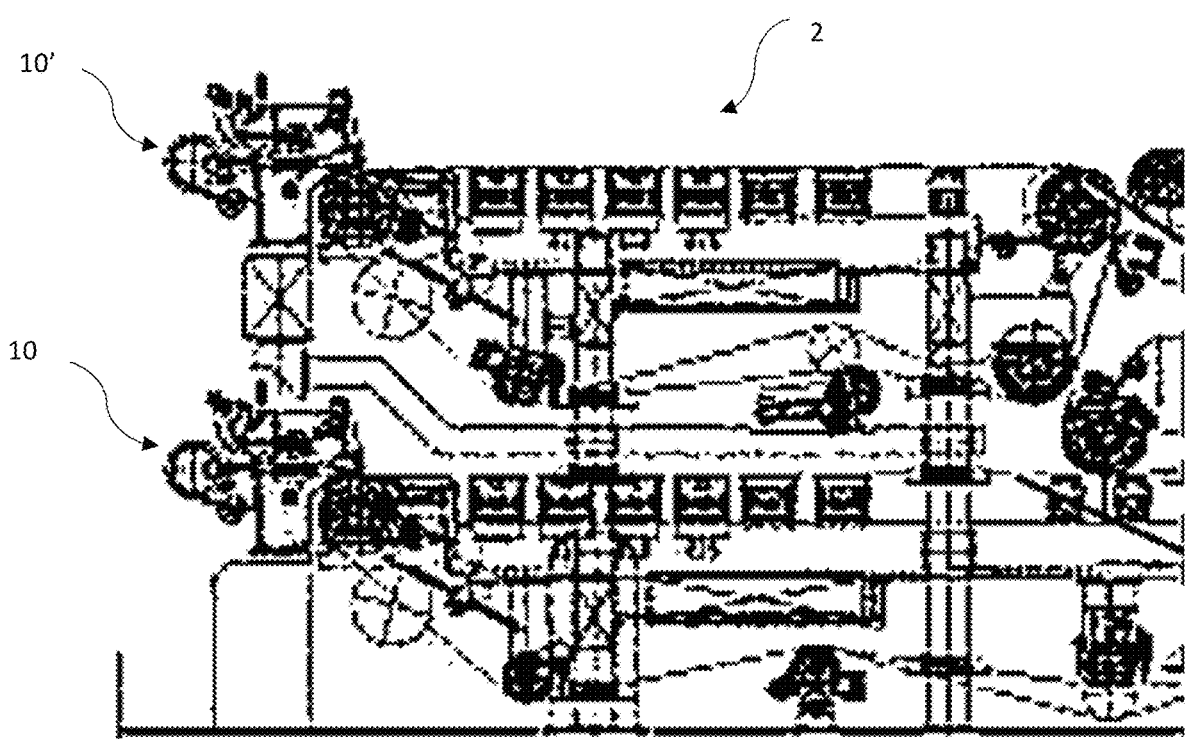
FIG. 19 is a wet end of a paper machine having two headboxes.

FIG. 19 illustrates a paper machine 2 having a first head box 10 and a second head box 10' both of which may be equipped with the monitoring system taught herein.

Variation 1 comprises: a formation detection system comprising: (a) one or more sensors and (b) one or more lights that illuminate a location of interest so that the one or more sensors can monitor the location of interest; wherein one of the one or more sensors are located substantially planar with a wire of a paper machine and proximate to a slice opening so that the one of the one or more sensors is adjacent to a cut through so that the one of the one or more sensors is capable of measuring stock above the wire and removed water below the wire, and wherein the one of the one or more sensors is capable of measuring a distance between an impingement location of a stock jet and the wire from a forming board.

Variation 2 may include variation 1 and may further comprise: a distance of the stock jet extending through the wire is measured.

Variation 3 may include any of variations 1-2 and may further comprise: the impingement location is varied depending upon formation monitored on the wire by the formation detection system.

Variation 4 may include any of variations 1-3 and may further comprise: the distance of the stock jet extending through the wire is increased or decreased by varying pressure of the stock jet or impingement angle so that formation on the wire is varied.

Variation 5 may include any of variations 1-4 and may further comprise: a second of the one or more sensors is capable of monitoring surface topography of the stock above the wire.

Variation 6 may include any of variations 1-5 and may further comprise: one or more of the one of the one or more lights is located above the wire and one or more of the one of the one or more lights is located below the wire.

Variation 7 may include any of variations 1-6 and may further comprise: the formation detection system is capable of comparing a location of stock monitored by the one of the one or more sensors and the second of the one or more sensors and the formation detection system is capable of tracking the location along the paper machine as the location travels in the machine direction.

Variation 8 comprises: a method comprising: (a) monitoring a wire proximate to a slice opening with one or more sensors so that a location above the wire is monitored and a location below the wire is monitored; (b) locating a location where a stock jet impinges with the wire; (c) locating a distal tip of a forming board or a distal tip of a first foil from the slice opening; and (d) measuring a distance between the location where the stock impinges with the wire and the distal tip of the forming board or the distal tip of the first foil.

Variation 9 may include any of variations 1-8 and may further comprise: adjusting the distance between the location where the stock impinges with the wire and the distal tip of the forming board or the distal tip of the first foil.

Variation 10 may include any of variations 1-9 and may further comprise: adjusting an angle of the stock jet relative to the wire.

Variation 11 may include any of variations 1-10 and may further comprise: moving the forming board or the first foil.

Variation 12 may include any of variations 1-11 and may further comprise: the forming board or the first foil are moved in the machine direction or toward or away from the wire.

Variation 13 may include any of variations 1-12 and may further comprise: measuring a distance the stock jet extends through the wire at the location where the stock jet impinges with the wire.

Variation 14 may include any of variations 1-13 and may further comprise: adjusting a pressure of the stock jet or an angle of the stock jet relative to the wire.

Variation 15 may include any of variations 1-14 and may further comprise: adjusting a speed of the wire.

Variation 16 comprises: a formation detection system comprising: (a) two or more sensors wherein the two or more sensors include: (i) a first of the two or more sensors is directed to a location along a paper machine corresponding to a first sheet of paper and (ii) a second of the two or more sensors is directed to a location along a paper machine corresponding to a second sheet of paper; (b) two or more lights; and (c) a control system; wherein formation of the first sheet of paper and formation of the second sheet of paper are matched up by the control system to form joint data so that when the first sheet of paper and the second sheet of paper are joined, formation data regarding the first sheet of paper and the second sheet of paper is recorded individually.

Variation 17 may include any of variations 1-16 and may further comprise: the two or more sensors include a third sensor that is capable of monitoring a location where the first sheet of paper and the second sheet of paper are joined to form a single sheet.

Variation 18 may include any of variations 1-17 and may further comprise: the control system compares data from the third sensor to the joined data so that formation of the single sheet is generated and any formation issues within the single sheet can be tracked to the first sheet or the second sheet.

Variation 19 may include any of variations 1-18 and may further comprise: the two or more lights are located on a same side of a sheet of paper as the two or more sensors.

Variation 20 may include any of variations 1-19 and may further comprise: wherein one or more of the two or more lights are located on a different side of a sheet of paper as the two or more sensors.

Variation 21 may include any of variations 1-20 and may further comprise: wherein the two or more lights are located on both a first side and a second side of a sheet of paper on the paper machine.

Variation 22 may include any of variations 1-21 and may further comprise: the two or more sensors include a fourth sensor that is located after all or a portion of a press section so that formation of the single sheet is measured.

Variation 23 may include any of variations 1-22 and may further comprise: formation measured by the fourth sensor is compared to formation measured by the first sensor, second sensor, and third sensor so that the paper machine can be adjusted upstream of the first sensor, the second sensor, the third sensor, or a combination thereof to remove any detected formation issues.

Variation 24 comprises: a method comprising: (a) monitoring formation of a first ply with a first sensor of a plurality of sensors; (b) monitoring formation of a second ply with a second sensor of the plurality of sensors; and correlating the formation monitored by the first sensor with the formation monitored by the second sensor.

Variation 25 may include any of variations 1-24 and may further comprise: wherein the step of correlating comprises matching up the first ply with the second ply so that when the first ply and the second ply are combined the correlated formation predicts combined formation.

Variation 26 may include any of variations 1-25 and may further comprise: monitoring formation the first ply and the second ply when the first ply and the second ply are combined to form a single sheet with a third sensor of the plurality of sensors.

Variation 27 may include any of variations 1-26 and may further comprise: comparing the formation correlated to the formation monitored by the third sensor.

Variation 28 may include any of variations 1-27 and may further comprise: adjusting a paper machined based upon differences in the formation correlated and measured formation.

Variation 29 may include any of variations 1-28 and may further comprise: comparing formation defects to the formation from the first sensor and the second sensor to ascertain if the formation defect is in the first ply or the second ply.

Variation 30 may include any of variations 1-29 and may further comprise: adjusting the paper machine to change formation of the first ply, the second ply, or both based upon detection of the first ply, the second ply, or both.

Variation 31 may include any of variations 1-30 and may further comprise: a control system that receives the formation from the first sensor, the second sensor, the third sensor, or both Variation 32 comprises: a formation detection system comprising: (a) one or more sensors and (b) one or more lights that illuminate a location of interest so that the one or more sensors can monitor the location of interest; wherein one of the one or more sensors are located within a press section of a paper machine, a dryer section, or both and the one or more lights monitor formation of a sheet of paper within the press section, the dryer section, or both.

Variation 33 may include any of variations 1-32 and may further comprise: one or more of the one or more sensors monitor a nip between two press rolls or a transfer location between two dryer cans.

Variation 34 may include any of variations 1-33 and may further comprise: the one or more of the one or more sensors is located above the sheet of paper, below the sheet of paper, or the one or more sensors are located both above and below the sheet of paper.

Variation 35 may include any of variations 1-34 and may further comprise: the one or more of the one or more sensors monitor an upstream side of the nip of the two press rolls or the transfer location between the two dryer cans, on a down stream side of the two press rolls or the two dryer cans, or both.

Variation 36 may include any of variations 1-35 and may further comprise: one or more of the one or more lights are located below the sheet of paper.

Variation 37 may include any of variations 1-36 and may further comprise: one of the one or more sensors is an overhead sensor that views the sheet from a location substantially normal to the sheet of paper.

Variation 38 may include any of variations 1-37 and may further comprise: the one or more sensors is located upstream of two press rolls, between two sets of press rolls, after the press section, upstream of two dryer cans, between two sets of dryer cans, after the dryer section, or a combination thereof.

Variation 39 may include any of variations 1-38 and may further comprise: the one or more sensors are located above the sheet, below the sheet, or both.

Variation 40 may include any of variations 1-39 and may further comprise: the one or more sensors monitor an entire cross-machine of a paper machine, the one or more sensors span the cross-machine of a paper machine to monitor an entire cross machine, the one or more sensors are movable along a cross-machine, or a combination thereof.

Variation 41 may include any of variations 1-40 and may further comprise: the formation detection system includes a control system and the control system combines one or more measurements or one or more pieces of data to create one formation illustration that extends the entire cross-machine direction of the paper machine.

Variation 42 may include any of variations 1-41 and may further comprise: the one or more sensors monitor surface characteristics in addition to formation of the sheet.

Variation 43 may include any of variations 1-42 and may further comprise: the surface characteristics include wire marks, dandy roll marks, felt marks, embossment, flocks of fibers, or a combination thereof.

Variation 44 may include any of variations 1-43 and may further comprise: the one or more sensors are a camera.

Variation 45 comprises a method comprising: (a) monitoring a sheet of paper with one or more sensors at one or more locations along a paper machine as the sheet of paper extends between two press rolls or two sets of press rolls of a press section or between two dryer cans a dryer section; (b) monitoring formation of the sheet of paper; and (c) monitoring surface characteristics of the sheet of paper.

Variation 46 may include any of variations 1-45 and may further comprise: monitoring formation of the sheet of paper includes measuring a distance between flocks of fibers within the sheet.

Variation 47 may include any of variations 1-46 and may further comprise: monitoring formation monitors shrinkage of the sheet of paper.

Variation 48 may include any of variations 1-47 and may further comprise: the shrinkage of the sheet of paper is a difference between a cross-machine width of the sheet of paper at a first location and a cross-machine width of the sheet of paper at a second location.

Variation 49 may include any of variations 1-48 and may further comprise: the difference is compared to a grade of paper being run and then the difference is compared to a look up table for differences in prior runs.

Variation 50 may include any of variations 1-49 and may further comprise: adjusting an amount of pressure exerted by the two press rolls, the temperature of dryer cans within the dryer section, or both.

Variation 51 may include any of variations 1-50 and may further comprise: adjusting speed of the paper machine.

Variation 52 may include any of variations 1-51 and may further comprise: monitoring a nip location between the two press rolls.

Variation 53 may include any of variations 1-52 and may further comprise: monitoring a location above the sheet of paper, a location below the sheet of paper, or both as the sheet of paper extends into the nip between the two press rolls, extending out of the nip between the two press rolls, or both.

Variation 54 may include any of variations 1-53 and may further comprise: the one or more sensors monitor the sheet of paper at an angle as the sheet of paper extends into the nip or out of the nip and the angle is about 5 degrees or more and about 85 degrees or less, preferably about 15 degrees or more and about 75 degrees or less, or more preferably about 30 degrees or more and about 60 degrees or less (i.e., about 45 degrees).

Variation 55 may include any of variations 1-54 and may further comprise: the one or more sensors monitor the sheet of paper before the sheet of paper enters the dryer section, after the sheet of paper exits the dryer section, or both.

Variation 56 may include any of variations 1-55 and may further comprise: one of the one or more sensors is located periodically between the two dryer cans.

Variation 57 may include any of variations 1-56 and may further comprise: periodically is two or more dyer cans apart and 20 or less dryer cans apart or preferably 3 or more dryer cans apart and 15 or less dryer cans apart.

Variation 58 may include any of variations 1-57 and may further comprise: the one or more seniors extend at an angle relative to the sheet of paper as the sheet of paper extends between the two dryer cans and the angle is about 5 degrees or more and about 85 degrees or less, preferably about 15 degrees or more and about 75 degrees or less, or more preferably about 30 degrees or more and about 60 degrees or less (i.e., about 45 degrees).

Variation 59 may include any of variations 1-58 and may further comprise: one of the one or more sensors is normal to the sheet of paper.

Variation 60 may include any of variations 1-59 and may further comprise: one or more lights are located above the sheet, one or more lights are located below the sheet, or both.

Variation 61 may include any of variations 1-60 and may further comprise: the surface characteristics of the sheet of paper is include wire marks, dandy roll marks, felt marks, embossment, flocks of fibers, surface topography, or a combination thereof.

Variation 62 may include any of variations 1-61 and may further comprise: a depth of the surface characteristics is monitored.

Variation 63 may include any of variations 1-62 and may further comprise: adjusting pressure of the press section, adjusting temperature of the dryer section, adjusting pressure of a felt in the press section, adjusting pressure of a felt in the dryer section, or a combination thereof based upon the depth of the surface characteristics.

Variation 64 may include any of variations 1-63 and may further comprise: changing slice opening characteristics, rush/drag, cut-through characteristics, or a combination thereof based upon the monitored surface characteristics.

Variation 65 comprises: a formation detection system comprising: (a) one or more sensors and (b) one or more lights that illuminate a location of interest so that the one or more sensors can monitor the location of interest; and wherein the one or more sensors are located within a calender section and monitor formation, surface characteristics, or both of a sheet of paper at one or more locations within the calender section.

Variation 66 may include any of variations 1-65 and may further comprise: one or more of the one or more sensors monitor the sheet of paper as the sheet of paper extends into the calender section, exits the calender section, or both.

Variation 67 may include any of variations 1-66 and may further comprise: the calender section includes one or more nips and one or more of the one or more sensors monitor the sheet of paper extending into the one or more nips, exiting the one or more nips, or both.

Variation 68 may include any of variations 1-67 and may further comprise: the formation detection system includes a control system and the control system is configured to compare the formation, the surface characteristics, or both of the sheet of paper extending into the nip and exiting the nip so that a change in the formation, change in the surface characteristics, or both can be compared.

Variation 69 comprises: a method comprising: (a) monitoring a sheet of paper with one or more sensors at one or more location along a paper machine as the sheet of paper extends into a calender section; (b) monitoring formation of the sheet of paper within the calender section; and (c) monitoring surface characteristics of the sheet of paper within the calender section.

Variation 70 may include any of variations 1-69 and may further comprise: comparing the formation, the surface characteristics, or both of the sheet of paper entering the calender section and exiting the calender section.

Variation 71 may include any of variations 1-70 and may further comprise: determining a change in the formation, the surface characteristics, or both and determining if any changes are needed in the calender section.

Variation 72 may include any of variations 1-71 and may further comprise: adjusting pressure of one or more calender rolls based upon the changes in the formation, the surface characteristics, or both.

Variation 73 may include any of variations 1-72 and may further comprise: monitoring the sheet of paper as the sheet of paper enters one or more nips in the calender section, exits the one or more nips in the calender section, or both.

Variation 74 may include any of variations 1-73 and may further comprise: determining formation changes, surface characteristic changes, or both of the sheet of paper from passing through the one or more nips in the calender section.

Variation 75 may include any of variations 1-74 and may further comprise: changing an amount of fluids added to the calender section, an amount of pressure applied by one or more calender rolls within the calender section, a speed of one or more of the calender rolls within the calender section, or a combination thereof.

Variation 76 may include any of variations 1-75 and may further comprise: based upon the change in the formation the surface characteristics, or both one or more calender rolls are changed, fixed, or both.

Variation 77 may comprise: a formation detection system comprising: (a) one or more sensors and (b) one or more lights that illuminate a location of interest so that the one or more sensors can monitor the location of interest; and wherein the one or more sensors are located within a reel section and monitor formation, surface characteristics, or both of a sheet of paper at one or more locations within the reel section.

Variation 78 may include any of variations 1-77 and may further comprise: the one or more sensors monitor the sheet of paper as the sheet of paper is wound unto the reel, before the sheet of paper is wound unto the reel, or both.

Variation 79 may include any of variations 1-78 and may further comprise: the formation detection system includes a control system and the control system monitors a profile of the reel in the cross-machine direction so that the cross-machine of the sheet of paper on the reel has a substantially even profile while winding.

Variation 80 comprises: a method comprising: (a) monitoring a sheet of paper with one or more sensors at one or more location along a paper machine as the sheet of paper extends into a reel section; (b) monitoring formation of the sheet of paper within the reel section; and (c) monitoring surface characteristics of the sheet of paper within the reel section.

Variation 81 comprises: a formation detection system comprising: (a) two or more sensors; (b) two or more lights that illuminate a location of interest, each of the two or more lights being located directly opposite one of the two or more sensors so that the one of the two or more sensors monitors the location of interest illuminated by each of the two or more lights; wherein a first of the two or more sensors is located in or after a wet end of a paper machine and a second of the two or more sensors is located in or before a press section of the paper machine.

Variation 82 may include any of variations 1-81 and may further comprise: the two or more sensors and the two or more lights include a third sensor and a third light located before or within a dryer section.

Variation 83 may include any of variations 1-82 and may further comprise: the two or more sensors and the two or more lights include a fourth sensor and a fourth light located before or within a calender section.

Variation 84 may include any of variations 1-83 and may further comprise: the two or more sensors and the two or more lights include a fifth sensor and a fifth light located before or within a reel section.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of or even consists of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 Paper machine
3 Slice opening
4 Headbox
5 Breast roll
6 Wire
7 Forming Board
8 Foil sections
9 Foil
9A Angle adjustable foil
9B Height adjustable foil
9C Static Foils
10 Couch roll
11 Removed water
12 Dry Line
14 Machine Direction
16 Stock jet
18 Wet end
20 Monitoring system
22 Light
24 sensor
26 High angle sensors
28 Low angle sensor
30 Formation Detection System
32 Multi-ply sensors
34 Press Section Sensors
36 Dryer Section Sensors
40 Control System
42 Controller
44 Formation Monitor
46 Graphical Formation Representation
48 Formation Change
50 Numerical Formation Representation
60 Stock
62 Fiber
64 Water
70 Monitoring region
72 Cut through
76 Wet line
78 Stock activity line
80 Sheet
82 Pin Hole
84 Streak
86 Pulsation
88 Flakes
90 Bubble or Drop
92 Light
94 Dark
100 Press section
102 Press Roll
104 Overhead sensor
106 High angle sensor
108 Low angle sensor
110 Nip
120 Dryer Section
122 Dryer Cans
124 Transfer location
126 Transfer sensor
130 Calender Section
132 Calender roll
134 Nip sensor
140 Reel Section
142 Reel

We claim:
1. A formation detection system comprising:
 a. one or more sensors, wherein at least one of the one or more sensors is a camera and
 b. one or more lights that illuminate a location of interest so that the one or more sensors can monitor the location of interest;
 wherein one of the one or more sensors is located at a beginning of a press section of a paper machine, a dryer section, or both and at an end of the press section of a paper machine, a dryer section, or both, and wherein the one or more lights illuminate a sheet of paper at the beginning of the press section, the dryer section, or both and at the end of the press section of a paper machine, a dryer section, or both so that the one or more sensors are capable of monitoring formation of the sheet of paper within the press section, the dryer section, or both.

2. The formation detection system of claim 1, wherein one or more of the one or more sensors monitor a nip between two press rolls of the press section or a transfer location between two dryer cans of the dryer section.

3. The formation detection system of claim 2, further comprising:
one or more sensors-located between two sets of press rolls in the press section, between two sets of dryer cans in the dryer section, or both.

4. The formation detection system of claim 1, wherein the one of the one or more sensors is located above the sheet of paper, below the sheet of paper, or the one or more sensors are located both above and below the sheet of paper.

5. The formation detection system of claim 1, wherein one or more of the one or more lights are located below the sheet of paper, and wherein one of the one or more sensors is an overhead sensor that views the sheet from a location substantially normal to the sheet of paper.

6. The formation detection system of claim 1, wherein at least one of the one or more sensors is located normal to the sheet of paper so that the one of the one or more sensors monitor surface characteristics in addition to formation of the sheet.

7. The formation detection system of claim 1, wherein the at least one of the one or more sensors that is the camera on a first side of the sheet of paper and one of the one or more lights are located on a second side of the sheet of paper and aligned with the camera so light from the one or more lights is directed through the sheet of paper towards the camera.

8. A formation detection system comprising:
a. two or more sensors wherein the two or more sensors include:
 i. a first of the two or more sensors is directed to a location along a paper machine corresponding to a first sheet of paper and
 ii. a second of the two or more sensors is directed to a location along a paper machine corresponding to a second sheet of paper;
b. two or more lights located adjacent to the two or more sensors; and
c. a control system;
wherein formation of the first sheet of paper and formation of the second sheet of paper are matched up by the control system to form joint data so that when the first sheet of paper and the second sheet of paper are joined, formation data regarding the first sheet of paper and the second sheet of paper is recorded individually; and
wherein the first of the two or more sensors and the second of the two or more sensors comprise a camera that monitors the formation of the first sheet of paper and the formation of the second sheet of paper respectively.

9. The formation detection system of claim 8, wherein the two or more sensors include a third sensor that is capable of monitoring a location where the first sheet of paper and the second sheet of paper are joined to form a single sheet, and wherein the control system compares data from the third sensor to the joined data so that formation of the single sheet is generated and any formation issues within the single sheet can be tracked to the first sheet or the second sheet.

10. The formation detection system of claim 8, wherein one or more of the two or more lights are located on a different side of a sheet of paper as the two or more sensors, or the two or more lights are located on both a first side and a second side of a sheet of paper on the paper machine.

11. The formation detection system of claim 8, wherein the two or more sensors include a fourth sensor that is located after all or a portion of a press section so that formation of the single sheet is measured.

12. The formation detection system of claim 11, wherein formation measured by the fourth sensor is compared to formation measured by the first sensor, second sensor, and third sensor so that the paper machine can be adjusted upstream of the first sensor, the second sensor, the third sensor, or a combination thereof to remove any detected formation issues.

* * * * *